US006994982B1

(12) United States Patent
Watt et al.

(10) Patent No.: US 6,994,982 B1
(45) Date of Patent: Feb. 7, 2006

(54) ISOLATING BIOLOGICAL MODULATORS FROM BIODIVERSE GENE FRAGMENT LIBRARIES

(75) Inventors: Paul Michael Watt, Mt. Claremont (AU); Wayne Robert Thomas, Nedlands (AU)

(73) Assignee: Phylogica Limited, Subiaco (AU)

( * ) Notice: Subject to any disclaimer, the term of this patent is extended or adjusted under 35 U.S.C. 154(b) by 0 days.

(21) Appl. No.: 09/568,229

(22) Filed: May 5, 2000

Related U.S. Application Data

(60) Provisional application No. 60/132,711, filed on May 5, 1999.

(51) Int. Cl.
*G01N 33/569* (2006.01)

(52) U.S. Cl. .................. 435/7.37; 435/7.32; 435/7.31; 435/7.1; 435/6; 435/4; 435/DIG. 15; 435/DIG. 14; 435/7.92

(58) Field of Classification Search ............... 435/7.92, 435/7.37, 7.32, 7.2, 7.1, 6, 5, DIG. 15, DIG. 14
See application file for complete search history.

(56) References Cited

U.S. PATENT DOCUMENTS

| 5,516,637 | A | | 5/1996 | Huang et al. |
|---|---|---|---|---|
| 5,763,239 | A | | 6/1998 | Short et al. |
| 5,783,431 | A | * | 7/1998 | Peterson et al. ............ 435/455 |
| 5,821,047 | A | | 10/1998 | Garrard et al. |
| 6,083,715 | A | | 7/2000 | Georgiou et al. |
| 6,174,673 | B1 | * | 1/2001 | Short et al. ..................... 435/6 |
| 6,190,908 | B1 | | 2/2001 | Kang |
| 6,238,884 | B1 | * | 5/2001 | Short et al. ................ 435/69.1 |
| 6,297,004 | B1 | | 10/2001 | Russell et al. |
| 6,316,223 | B1 | | 11/2001 | Payan et al. |
| 6,319,690 | B1 | | 11/2001 | Little et al. |
| 6,361,969 | B1 | | 3/2002 | Galeotti |
| 6,583,275 | B1 | * | 6/2003 | Doucette-Stamm et al. ......................... 536/23.1 |
| 2002/0150906 | A1 | | 10/2002 | Debe |
| 2003/0215846 | A1 | | 11/2003 | Watt et al. |

FOREIGN PATENT DOCUMENTS

| AU | 18603/95 | 6/1995 |
|---|---|---|
| AU | 48085/97 | 4/1998 |
| AU | 22587/99 | 7/1999 |
| WO | WO 95/17412 | 6/1995 |
| WO | WO 98/16835 | 4/1998 |
| WO | WO 99/35282 | 7/1999 |

OTHER PUBLICATIONS

Balaban et al. "Autoinducer of Virulence as a Target for Vaccine and Therapy Against Staphylococcus aureus," *Science*, vol. 280 (Apr. 17, 1998): pp. 438-440.

Colas et al. "Genetic selection of peptide aptamers that recognize and inhibit cyclin-dependent kinase 2," *Nature*, vol. 380 (Apr. 11, 1996): pp. 548-550.

Derossi et al. "The Third Helix of the Antennapedia Homeodomain Translocates through Biological Membranes," *The Journal of Biological Chemistry*, vol. 269, No. 14 (1994): pp. 10444-10450.

Fahraeus et al. "Inhibition of pRb phosphoryletion and cell-cycle progression by a 20-residue peptide derived from $p16^{CDKN2/INK4N}$," *Current Biology*, vol. 6, No. 1 (1996): pp. 84-91.

Kolonin et al. "Targeting cyclin-dependent kinases in Drosophia with peptide aptamers," *Pro. National Academy of Science*, vol. 94, (Nov. 1998): pp. 14266-14271.

Leitner et al. "A mimotope defined by phage display inhibits IgE blinding to the plant panallergen profiling," *European Journal of Immunology*, vol. 28 (1998): pp. 2921-2927.

Marcello et al. "Specific inhibition of herpes virus replication by receptor-mediated entry of an antiviral peptide linked to Escherichia coli enterotoxin B subunit," *Proc. National Academy of Science*, vol. 91 (Sep. 1994): pp. 8994-8998.

Mennuni et al. "Identification of a Novel Type 1 Diabetes-specific Epitope by Screening Phage Libraries with Sera from Pre-diabetic Patients," *Journal of Molecular Biology*, vol. 268 (1997): pp. 599-606.

Phelan et al. "Intercellular delivery of functional p53 by the herpesvirus protein VP22," *Nature Biotechnology*, vol. 16 (May 1998): pp. 440-443.

Pincus et al. "Peptides that Mimic the Group B Streptococcal Type III Capsular Polysaccharide Antigen," *Journal of Immunology*, vol. 160 (1998): pp. 293-298.

Rocco et al. "Wide-Spectrum Antibiotic Activity of Synthetic, Amphipathic Peptides," *Biochemical and Biophysical Research Communications*, vol. 249 (1998): pp. 202-206.

Xu et al. "Cells that register logical relationships among proteins," *Proc. National Academy of Science*, vol. 94 (Nov. 1997): pp. 12473-12478.

Sambrook, et al. *Molecular Cloning: A Laboratory Manual*, 2nd Edition. Cold Spring Harbor Laboratory Press, U.S.A. (1989).

(Continued)

*Primary Examiner*—T. D. Wessendorf
(74) *Attorney, Agent, or Firm*—Morrison & Foerster LLP

(57) ABSTRACT

The present invention provides a method for identifying a modulator or mediator of a biological activity, which activity includes antigenicity and or immunogenicity, said method comprising the step of:
 (i) producing a gene fragment expression library derived from defined nucleotide sequence fragments; and
 (ii) assaying the expression library for at least an amino acid sequence derived from step (i) for a biological activity wherein that activity is different from any activity the amino acid sequence may have in its native environment.

13 Claims, No Drawings

OTHER PUBLICATIONS

Finley et al. "Targeting cyclin-dependent kinases in Drosophila with peptide aptamers," *Proc. Natl. Acad. Sci.*: pp. 14266-14271 (Nov. 1998).
Xu et al. "Cells that register logical relationships among proteins," *Proc. Natl. Acad. Sci.*: pp. 12473-12478 (Nov. 1997).
Pini et al. "Design and use of a phage display library," *Journal of Biological Chemistry*, vol. 273, issue 34: pp. 21769-21776 (Aug. 21, 1998).
McConnell et al. "Constrained peptide libraries as a tool for finding mimotopes," *Gene*, vol. 151: pp. 115-118 (1994).
Bremnes et al. "Selection of phage displayed peptides from a random 10-mer library recognizing a peptide target," *Immunotechnology*, vol. 4: pp. 21-28 (1998).
Burioni et al. "A new substraction technique for molecular cloning of rare antiviral antibody specificities from phage display libraries," *Res Virol*. vol. 149: pp. 327-330 (1998).
Pincus et al. "Peptides that mimic the group B streptococcal type III capsular polysaccharide antigen," *Journal of Immunology*, vol. 160: pp. 293-298 (1998).
Young, K.H. "Yeast two-hydrid: So many interactions, (in) so little time," *Biology of Reproduction*, vol. 58: pp. 302-311 (1998).
Colas et al. "Genetic selection of peptide aptamers that reconize and inhibit cyclin-dependent kinase 2," *Nature*, vol. 380: pp. 548, 550 (Apr. 11, 1996).
Leitner A. et al. "A mimotope defined by phage display inhibits lgE binding to the plant panallergen profiling" EUR. J. Immunol., vol. 28, -1998 pp. 2921-2927.
Caponigro, G. et al., "Transdominant genetic analysis of a growth control pathway," *Proc. Natl. Acad. Sci. USA*, vol. 95, pp. 7508-7513 (Jun. 1998).
Amann and Brosius, Gene 40:183190 (1985).
Baud and Karlin, PNAS 96: 12494-12499 (1999).
Berzofky, Science 229:932-940 (1985).
Blum, et al., PNAS 97:2241-2246 (2000).
Bonaldo, et al., Genome Res. 6:791-806 (1996).
Britten and Kohne, Science 161:529-540 (1968).
Campbell, et al., Biochem. 36:12791-12801 (1997).
Caponigro, et al., Proc Natl Acad Sci. USA 95:7508-7513 (1998).
Chapman, et al., J. Immunol. 133:2488-2495 (1984).
Colbère-Garapin, et al., J. Mol. Biol. 150:1-14 (1981).
de Soultrait, et al., J. Mol. Biol. 318:45-58 (2002).
Dent, et al., PNAS 97:2674-2679 (2000).
Devereauxe, et al., Nucl. Acids Res. 12:387-395 (1984).
DeVito, et al., Nature Biotechnology 20:478-483 (2002).
Faber, et al., Proc. Natl. Acad. Sci. USA 96:179-184 (1999).
Fabret, et al., Nucl. Acids Res. 28:e95 (2000).
Fehrsen and du Plesis, Immunotechnology 4:175-184 (1999).
FitzGerald, Drug Discovery Today 5:253-258 (2000).
Franzoni, et al., J. Biol. Chem. 272:9734-9741 (1997).
Gegg, et al., Protein Sci., 6:1885-1892 (1997).
Getzoff, et al., Science 235:1191-1196 (1987).
Greene and Thomas, et al., Mol Immunology 29:257-262 (1992).
Hengeveld, et al., Biochem. 41:7490-7500 (2002).
Heymann, et al., J. Allergy Clin. Immunol. 83:1055-1067 (1989).
Hofmann, et al., Proc. Natl. Acad. Sci. USA 93:5185-5190 (1996).
Hoogenboom, et al., Nucleic Acids Res 19:4133-4137 (1991).
Horng, Biochem. 41:13360-13369 (2002).
Houshmand, et al., Anal. Biochem. 268:363-370 (1999).
Humphrey and Chamberlin, Chem. Rev. 97:2243-2266 (1997).
Irbäck, et al., Proc. Natl. Acad. Sci. USA 93:9533-9538 (1996).
Kinzler and Vogelstein, Nucleic Acids Res. 17:3645-3653 (1989).
Koncz, et al., Proc. Natl. Acad. Sci. USA 84:131-135 (1987).
Kopczynski, et al., Proc. Natl. Acad. Sci. USA 95:9973-9978 (1998).
Lee, et al., Biochem. and Mol. Biology Int. 34:159-168 (1994).
Leslay, et al., J. Biol. Chem. 266:2632-2638 (1991).
Lind, et al., J. Immunol. 40:4256-4262 (1988).
Marsh, et al., Hum. Mol. Genet. 9:13-25 (2000).
McCafferty, et al., Nature 348:552-554 (1990).
Morris, et al., Curr. Opinion Biotech. 11:461-466 (2000).
Morris, et al., Nature Biotech. 19:1173-1176 (2001).
Mulligan and Berg, Proc. Natl. Acad. Sci. USA 78:2072-2076 (1981).
Needleman and Wunsch, J. Mol. Biol. 48:443-453 (1970).
Neidigh, et al., Nature Structure Biology 9:425-430 (2002).
Ness, et al., Nature Biotechnology 20:1251-1255 (2002).
Norman, et al., Science 285:591-595 (1999).
O'Hare, et al., Proc. Natl. Acad. Sci. USA 78:1527-1531 (1981).
Palzkill, et al., Gene 221:79-83 (1998).
Pande, et al., Proc. Natl. Acad. Sci. USA 91:12972-12975 (1994).
Read, et al., Drug Disc. Today 6:887-892 (2001).
Richter, et al., Protein Expression and Purification 19:375-383 (2000).
Robben, et al., J. Biol. Chem. 277:17544-17547 (2002).
Roberts and Szostak, Proc. Natl. Acad. Sci. USA 94:12297-12302 (1997).
Rogers, et al., Mann. Genome 8:711-713 (1997).
Sali and Blundell, J. Mol. Biol. 234:779-815 (1993).
Sambook, et al., Molecular Cloning: A Laboratory Manual, 2nd Edition. Cold Spring Harbor Laboratory Press, USA, Chapter 12 & 13 (1989).
Santerre, et al., Gene 30:147-156(1984).
Satyal, et al., PNAS 97:5750-5755 (2000).
Shafikhani, et al., BioTechniques 23:304-310 (1997).
Shimatake and Rosenberg, Nature 292:128-132 (1981).
Sieber, et al., Nature Biotechnology 19:456-460 (2001).
Soares, Curr. Opinion Biotechnol. 8:542-546 (1997).
Strenglin, et al., EMBO Journal, 7:1053-1059 (1988).
Studier and Moffatt, J. Mol. Biol. 189:113-130 (1986).
Sugita, et al., Cancer Res. 62:3971-3979 (2002).
Thomas et al., Infect. and Immunol. 58:1909-1913 (1990).
Tokmakov, et al., Biochem. Biophys. Res. Comm. 236:243-247 (1997).
Tokmakov, et al., Biochem. Biophys. Res. Comm. 252:214-219 (1998).
Tripet, et al., J. Biol Chem. 272:8946-8956 (1997).
Van Regenmortel, Immunology Today 10:266-272 (1989).
Vidal and Legrain, Nucl. Acid Res. 27:919-929 (1999).
Vranken, et al., Proteins 47:14-24 (2002).
Wigler, et al., Proc. Natl. Acad. Sci. USA 77:3567-3570 (1980).
Wong, et al., Nucleic Acids Res. 24:3778-3783 (1996).
Xu, et al., Nature Genetics 27:23-29 (2001).

Yang, et al., J. Mol. Biol. 301:691-711 (2000).
Yang, et al., Biochem. 38:465477 (1999).
Yang, et al., Infect. and Immun. 66:3349-3354 (1998).
Yashueda, et al., Clin. Exp. Allergy. 26:171-177 (1996).
Zhang, et al., Proc. Natl. Acad. Sci. USA 89:5847-5851 (1992).
Chong and Mandel, In: Bartel and Fields, The Yeast Two-Hydrid System, New York, NY pp. 289-297 (1997).
McConnell, et. al., Gene 151:115-118 (1994).
Arenkov, P. et al. (2000). "Protein Microchips: Use for Immunoassay and Enzymatic Reactions," *Analytical Biochemistry* 278:123-131.
Fillip, S.R. (2001). "The Role of *murMN* Operon in Penicillin Resistance and Antibiotic Tolerance of *Streptococcus pneumoniae,*" *Microbial Drug Resistance* 7(4):303-316.
Hosen, N. et al. (2004). "Identification of a Gene Element Essential for Leukemia-Specific Expression of Transgenes," *Leukemia* 18:415-419.
Lambros, C. et al. (Jun. 1979). "Synchronization of Plasmodium Falciparum Erythrocytic Stages in Culture," *J. Parasitol.* 65(3):418-420.
Maidhof, H. et al. (Jun. 1991). "*femA*, Which Encodes a Factor Essential for Expression of Methicillin Resistance, Affects Glycine Content of Peptidoglycan in Methicillin-Resistant and Methicillin-Susceptible *Staphylococcus aureus* Strains," *Journal of Bacteriology* 173(11):3507-3513.
Pavlickova, P. et al. (2003). "Microarray of Recombinant Antibodies Using a Streptavidin Sensor Surface Self-Assembled onto a Gold Layer," *Bio Techniques* 34(1):124-130.
Theiss, H.D. et al. (2003). "Enhancement of Gene Transfer With Recombinant Adeno-Associated Virus (rAAV) Vectors into Primary B-Cell Chronic Lymphocytic Leukemia Cells by CpG-oligodeoxynucleotides," *Experimental Hematology* 31:1223-1229.
Behrens, A. et al. (Mar. 1999). "Amino-Terminal Phosphorylation of c-Jun Regulates Stress-Induced Apoptosis and Cellular Proliferation," *Nature Genetics* 21: 326-329.
Estus, S. et al. (Dec. 1994). "Altered Gene Expression in Neurons During Programmed Cell Death: Identification of c-Jun as Necessary for Neuronal Apoptosis," *The Journal of Cell Biology* 127(6):1717-1727.
Fang, Y. et al. (2002). "G-Protein-Coupled Receptor Microarrays," *ChemBioChem* 3:987-991.
Garcia, M. et al. (Mar. 15, 2002), "The Mitochondrial Toxin 3-Nitropropionic Acid Induces Striatal Neurodegeneration via a c-*Jun* N-Terminal Kinase/c-Jun Module," *The Journal of Neuroscience* 22(6):2174-2184.
Gargala, G. et al. (1999). "Enzyme Immunoassay Detection of *Cryptosporidium Parvum* Inhibition by Sinefungin in Sporozoite Infected HCT-8 Enterocytic Cells," *International Journal of Parasitology* 29:703-709.

Hegde, S. S. et al. (Mar. 9, 2001). "FemABX Family Members Are Novel Nonribosomal Peptidyltransferases and Important Pathogen-Specific Drug Targets," *The Journal of Biological Chemistry* 276(10):6998-7003.
Kabouridis, P. S. (Nov. 2003). "Biological Applications of Protein Transduction Technology," *Trends in Biotechnology* 21(11):498-503.
Lee, Y. et al. (2003). "Proteochip: A Highly Sensitive Protein Microarray Prepared by a Novel Method of Protein Immobilization for Application of Protein-Protein Interaction Studies," *Proteomics* 3:2289-2300.
Mazmanian, S. K. et al. (May 9, 2000). "*Staphylococcus Aureus* Sortase Mutants Defective in the Display of Surface Proteins and in the Pathogenesis of Animal Infections," *PNAS* 97(10):5510-5515.
Mazmanian, S. K. et al. (Jul. 30, 1999). "*Staphylococcus Aureus* Sortase, an Enzyme that Anchors Surface Proteins to the Cell Wall," *Science* 285:760-763.
McElveen, J. E. (1998). "Primary Sequence and Molecular Model of the Variable Region of a Mouse Monoclonal Anti-Der p 1 Antibody Showing a Similar Epitope Specificity as Human IgE," *Clinical an Experimental Allergy* 28: 1427-1434.
Nedelkov, D. et al. (2001). "Analysis of Native Proteins from Biological Fluids by Biomolecular Interaction Analysis Mass Spectrometry (BIA/MS): Exploring the Limit of Detection, Identification of Non-Specific Binding and Detection of Multi-Protein Complexes," *Biosensors & Bioelectronics* 16:1071-1078.
Nelson, R. W. et al. (2000). Biosensor Chip Mass Spectrometry: A Chip-Based Proteomics Approach, *Electrophoresis* 21:1155-1163.
Nemoto, N. et al. (1999). "Fluorescence Labeling of the C-Terminus of Proteins with a Puromycin Analogue in Cell-Free Translation Systems," *FEBS Letters* 462:43-46.
Rohrer, S. et al. (Aug. 1999). "The Essential *Staphylococcus Aureus* Gene *fmhB* is Involved in the First Step of Peptidoglycan Pentaglycine Interpeptide Formation," *Proc. Natl. Acad. Sci. USA* 96:9351-9356.
Rosenthal, P. J. et al. (Jul. 1996). "Antimalarial Effects fo Vinul Sulfone Cysteine Proteinase Inhibitors," *Antimicrobial Agents and Chemotherapy* 40(7): 1600-1603.
Stranden, A. M. et al. (Jan. 1997). "Cell Wall Monoglycine Cross-Bridges and Methicillin Hypersusceptibility in a *femAB* Null Mutant of Methicillin-Resistant *Staphylococcus Aureus,*" *Journal Bacteriology* 179(1):9-16.
Thumm, G. et al. (1997) "Studies on Prolysostaphin Processing and Characterization of the Lysostaphin Immunity Factor (Lif) of *Staphylococcus Simulans* Biovar *Staphylolyticus*" *Molecular Microbiolgy* 23(6):1251-1265.

* cited by examiner

SEQUENCE LISTING

<160> NUMBER OF SEQ ID NOS: 14

<210> SEQ ID NO 1
<211> LENGTH: 118
<212> TYPE: PRT
<213> ORGANISM: Drosophila sp.
<220> FEATURE:
<221> NAME/KEY: NON_CONS
<222> LOCATION: (18)..(117)
<223> OTHER INFORMATION: Xaa = any amino acid; 99 of the 100 Xaa's can
      be present or absent

<400> SEQUENCE: 1

Cys Arg Gln Ile Lys Ile Trp Phe Gln Asn Arg Arg Met Lys Trp Lys
 1               5                  10                  15

Lys Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa
        100                 105                 110

Xaa Xaa Xaa Xaa Xaa Cys
        115

<210> SEQ ID NO 2
<211> LENGTH: 8
<212> TYPE: DNA
<213> ORGANISM: Artificial Sequence
<220> FEATURE:
<223> OTHER INFORMATION: Description of Artificial Sequence: Synthetic
      linker

<400> SEQUENCE: 2 ggaattcc                                                                8

<210> SEQ ID NO 3
<211> LENGTH: 10
<212> TYPE: DNA
<213> ORGANISM: Artificial Sequence
<220> FEATURE:
<223> OTHER INFORMATION: Description of Artificial Sequence: Synthetic
      linker

<400> SEQUENCE: 3
cggaattccg                                                             10

<210> SEQ ID NO 4
<211> LENGTH: 12
<212> TYPE: DNA
<213> ORGANISM: Artificial Sequence
<220> FEATURE:
<223> OTHER INFORMATION: Description of Artificial Sequence: Synthetic
      linker

<400> SEQUENCE: 4
ccggaattcc gg                                                          12

<210> SEQ ID NO 5
<211> LENGTH: 10
<212> TYPE: DNA
<213> ORGANISM: Artificial Sequence
<220> FEATURE:
<223> OTHER INFORMATION: Description of Artificial Sequence: Synthetic
      linker

<400> SEQUENCE: 5
ccaagcttgg                                                             10

<210> SEQ ID NO 6
<211> LENGTH: 32
<212> TYPE: DNA
<213> ORGANISM: Artificial Sequence
<220> FEATURE:
<221> NAME/KEY: variation
<222> LOCATION: (25)..(32)
<223> OTHER INFORMATION: n=a/c/t/g
<223> OTHER INFORMATION: Description of Artificial Sequence: Synthetic
      primer

<400> SEQUENCE: 6
gactacaagg acgacgacga caagnnnnnn nn                                    32

<210> SEQ ID NO 7
<211> LENGTH: 35
<212> TYPE: DNA

```
<213> ORGANISM: Artificial Sequence
<220> FEATURE:
<221> NAME/KEY: variation
<222> LOCATION: (28)..(35)
<223> OTHER INFORMATION: n=a/c/t/g
<223> OTHER INFORMATION: Description of Artificial Sequence: Synthetic
      primer

<400> SEQUENCE: 7
attcccggga agcttatcaa tcaatcannn nnnnn                               35

<210> SEQ ID NO 8
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gagaggaatt cagactacaa ggacgacgac gacaag                              36

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gagagaattc ccgggaagct tatcaatcaa tca                                 33

<210> SEQ ID NO 10
<211> LENGTH: 17
<212> TYPE: DNA
<213> ORGANISM: Artificial Sequence
<220> FEATURE:
<221> NAME/KEY: variation
<222> LOCATION: (10)..(17)
<223> OTHER INFORMATION: n=a/c/t/g
<223> OTHER INFORMATION: Description of Artificial Sequence: Synthetic
      primer

<400> SEQUENCE: 10
gagaattcan nnnnnnn                                                   17

<210> SEQ ID NO 11
<211> LENGTH: 16
<212> TYPE: DNA
<213> ORGANISM: Artificial Sequence
<220> FEATURE:
<221> NAME/KEY: variation
<222> LOCATION: (9)..(16)
<223> OTHER INFORMATION: n=a/c/t/g
<223> OTHER INFORMATION: Description of Artificial Sequence: Synthetic
      primer

<400> SEQUENCE: 11
gagaattcnn nnnnnn                                                    16

<210> SEQ ID NO 12
<211> LENGTH: 92
<212> TYPE: DNA
<213> ORGANISM: Artificial Sequence
<220> FEATURE:
<223> OTHER INFORMATION: Description of Artificial Sequence: Synthetic
      adaptor
```

-continued

```
<400> SEQUENCE: 12
aattcaatca atcacacaca ggaggccacc atggatgcat gtgtgcacgt gcacacatgc         60
atccatggtg gcctcctgtg tgtgattgat tg                                      92

<210> SEQ ID NO 13
<211> LENGTH: 90
<212> TYPE: DNA
<213> ORGANISM: Artificial Sequence
<220> FEATURE:
<223> OTHER INFORMATION: Description of Artificial Sequence:  Synthetic
      adaptor

<400> SEQUENCE: 13
aattcaatca atcacacaca ggaggccacc atggatgcat gtgtgcatgc acacatgcat         60
ccatggtggc ctcctgtgtg tgattgattg                                         90

<210> SEQ ID NO 14
<211> LENGTH: 88
<212> TYPE: DNA
<213> ORGANISM: Artificial Sequence
<220> FEATURE:
<223> OTHER INFORMATION: Description of Artificial Sequence:  Synthetic
      adaptor

<400> SEQUENCE: 14
aattcaatca atcacacaca ggaggccacc atggatgcat gtgtgcgcac acatgcatcc         60
atggtggcct cctgtgtgtg attgattg                                           88
```

ISOLATING BIOLOGICAL MODULATORS FROM BIODIVERSE GENE FRAGMENT LIBRARIES

FIELD OF THE INVENTION

The present invention relates to the field of screening gene libraries, and more particularly to the generation and screening of natural domain libraries derived from organisms with known genomic sequences. Methods for increasing the diversity of such biodiverse gene fragment libraries further by mutagenesis procedures are described. The present invention also provides the means by which a wide range of peptide-based therapeutics, prophylactics and diagnostic reagents may be developed.

General

Those skilled in the art will appreciate that the invention described herein is susceptible to variations and modifications other than those specifically described. It is to be understood that the invention includes all such variation and modifications. The invention also includes all of the steps, features, compositions and compounds referred to or indicated in the specification, individually or collectively, and any and all combinations or any two or more of the steps or features.

The present invention is not to be limited in scope by the specific embodiments described herein, which are intended for the purpose of exemplification only. Functionally equivalent products, compositions and methods are clearly within the scope of the invention as described herein.

Bibliographic details of the publications numerically referred to in this specification are collected at the end of the description. All references cited, including patents or patent applications are hereby incorporated by reference. No admission is made that any of the references constitute prior art.

As used herein the term "derived from" shall be taken to indicative that a specific integer may be obtained from a particular source albeit not necessarily directly from that source.

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

BACKGROUND TO THE INVENTION

Biological interaction/activities, such as protein:protein interactions, antigen:antibody interactions, protein:nucleic interactions, protein:ligand interactions and nucleic acid:nucleic acid interactions are involved in a wide variety of processes occurring in living cells. For example, agonism and antagonism of receptors by specific ligands, antibody-antigen interactions, including drugs, hormones, second messenger molecules, etc. may effect a variety of biological processes such as gene expression, cellular differentiation and growth, enzyme activity, metabolite flow and metabolite partitioning between cellular compartments, amongst others. DNA:protein and RNA:protein interactions are well known for their effects in regulating gene expression in both prokaryotic and eukaryotic cells, in addition to being critical for DNA replication and in the case of certain viruses, RNA replication. In cases where the propagation of cells is deleterious such as the replication of a pathogen or of a cancer cell, agents which target biological interaction/activities or functional structures, are suitable candidates for therapy. For example, agents that block the function of membrane channels or disrupt cytoplasmic membranes by other means, are attractive targets for anti-microbial therapies against pathogens. Further, agents that interact with antigen-specific or non-specific functions of the immune system may provide immunological modulators or vaccines for allergy, autoimmunity, infectious disease, fertility and invenomation. For example, agents that have the antigenicity of microbial antigens, tumour antigens, allergens or autoantigens may be used for vaccines or immunotherapy.

Undesirable or inappropriate gene expression and/or cellular differentiation, cellular growth and metabolism may be also be attributable, at least in many cases, to biological interaction/activities involving the binding and/or activity of proteinaceous molecules, such as transcription factors, peptide hormones, receptor molecules and enzymes, amongst others. In these cases, therapies can be envisaged which block such inappropriate interactions and/or which block the formation of inappropriate cellular structures.

Production of Peptides by Recombinant DNA Techniques

Peptides that can mediate or interfere with a diverse range of biological functions include natural peptides and peptides synthesised to represent a portion or a modified portion of a molecular known to mediate a target function. One source of such peptides are random peptides libraries constructed with random (or semi-random) oligonucleotides ligated into cloning sites of a plasmid or phage vectors.

Vectors containing DNA encoding different peptides are transfected or transformed into bacteria or other hosts and cloned by standard plaque or colony purification procedures. Clones producing peptides with a desired activity can be isolated by a variety of screening or selection procedures which are fundamentally the same as the screening procedures used to detect polypeptides encoded by cDNA or cDNA fragments. These include the production of peptides as fusions with the coat proteins of bacteriophage or fusions with bacterial surface proteins so the peptides can be used as tags for affinity purification procedures; the production of peptides from hosts infected with phage or transformed with plasmids to produce arrays of colonies or plaques which can be screened for ligand-binding activity or biological activity such as inhibiting the growth target bacteria or inducing the activation of genes in target bacteria; and in positive selection strategies such as the two hybrid cloning systems, where the peptide produced in the host microorganism binds to target proteins to form complexes which activate the expression of the reporter genes cloned into the same host. One of the significant advantages of phage display technology is that it enables the construction of libraries with very large complexities—ie. $10^{10}$ to $10^{11}$ individual clones.

Likewise, in 'reverse two hybrid' or 'split two hybrid' systems, libraries of appropriately expressed peptides can be screened for blockers of particular protein/protein interactions, which in turn reduces the expression of counter selectable reporter genes encoding toxic products.

Modifications of Peptides for Utility and Optimisation

Once the active peptide or a ligand binding peptide has been identified they can be modified by a variety of procedures to optimise their utility. Modification may include: alterations in the amino acid residues which engage the target to improve their binding specificity and affinity; modifications which affect the display of the peptide including the valency of binding and constraint of particular conformations; and modifications to attach further functional moieties such as markers, toxins and co-activators.

Synthetic peptides can include residues other than the 20 amino acids found in nature and/or can be cyclised by means such as oxidation of flanking cysteine residues. In the case of peptides mimicking antibody epitopes, carriers containing the T-cell epitopes required to induce high affinity immune responses can be added by genetic techniques.

Example of Peptides that Modulate Biological Systems

Peptides can be applied as therapeutics or lead molecules for designing therapeutics for disease including infection, cancer and metabolic disorders as well as agents for vaccines and immunotherapy, transplantation and diagnostics. The potential usefulness of such peptides has been demonstrated by the following examples:

Peptide Antimicrobial Agents

The antimicrobial effect demonstrated by natural peptides produced by frogs and insects and artificially synthesised cationic peptides. A large variety of antibiotics are peptides or polypeptides. The granules of mammalian neutrophils produce families of antimicrobial polypeptides including azurocidin, cathepsin G and Cationic Antimicrobial Peptides (CAP57 and CAP37). In addition, neutrophils produce at least two families of antimicrobial peptides, the defensins and the bactenecins. Moreover, many natural antibiotics and antifungal drugs are composed of peptides. For example, the magainin family of antimicrobial α-helical peptides isolated from the skin of the African clawed toad, *Xenopus Laevis* form lethal pores in the cell membranes of certain microorganisms. Similarly, certain α-helical peptides derived from a variety of insect genera have antimicrobial activity. Recently, several rational design approaches have been used to isolate novel peptide antibiotics. For example, Tiozzo et al., used a "sequence template" approach in which candidate peptide sequences were designed from alignments of natural antimicrobial peptides [1]. The identification of virulence determinants in several pathogens presents other attractive targets for antimicrobial therapy. For example, Balaban and colleagues (2) have recently identified an autoinducer of virulence in *Staphylococcus aureus* that controls the production of bacterial toxins involved in pathogenesis. The toxin genes are induced by a regulatory RNA molecule, RNAIII that is induced by a threshold concentration of an endogenous protein RNAIII Activating Protein (RAP) [2]. Peptide inhibitors of RAP might be expected to act as virulence determinants. Indeed, a natural peptide inhibitor of RAP called RIP (RNAIII inhibiting peptide) is produced by a non-pathogenic strain of *Staphylococcus aureus* and appears to inhibit the RNAIII gene and to cause reduced virulence [2].

Peptide Modulators of Growth Regulation

The ability of peptides to affect key modulators of growth regulation has been demonstrated by Brent and colleagues who used two hybrid screening to identified constrained peptide 'aptamers' from combinatorial libraries which bind tightly to and inhibit the function of cyclin dependent kinase 2. This demonstrates the potential for treatment of neoplasms (3).

Peptides can exhibit exquisite specificity. For example, peptide aptamers have been identified which can discriminate between two closely related allelic varients of the Ras protein (4). Moreover, a peptide aptamer against human cyclin dependent kinase 2 inhibits kinase activity exclusively on certain particular substrates.

Peptide specificity has also been demonstrated in vivo. In a recent report, expression of aptamers that recognised cyclin dependent kinases in transgenic flies was shown to cause developmental abnormalities in a dominant negative fashion (5). Importantly, the specificity of the two aptamers for particular Cdks (as determined by yeast two hybrid assays) was retained in the Drosophila in vivo assay. Moreover co-expression of the specific aptamer target Cdk suppressed the developmental phenotype observed (5). This report of successful targeted inhibition of an enzyme in vivo with aptamers, firmly establishes as practicable the principle for developing new therapeutic strategies based on interfering peptides.

Peptide-Based Inhibition: An Emerging Therapeutic Strategy

Much attention has recently focussed on peptides as potential therapeutic agents because they can be highly specific and readily synthesised. Phase display technologies are beginning to prove useful for providing peptide leads in drug discovery programs. Efficient delivery of peptide from outside the cell to the nucleus of eukaryotic cells can now be achieved by attaching sequences such as the targeting motif "penetratin" which is derived from the Drosophila Antennapaedia protein. More recently a family of such targeting peptides has been identified (6). For example, conjugation of peptide sequences to the VP22 protein has been shown to allow efficient export of the fusion protein to the nuclei of cells adjacent to primary transfectants (7). Several recent developments make it feasible to physically select conformationally constrained peptide domains in order to identify peptides that bind with very high affinity in vivo, favouring high potency. Mimetic peptides have been reported to inhibit protein interactions and/or enzyme function. Examples include a nonapeptide derived from the ribonucleotide reductase of herpes simplex virus that was linked to an enterotoxin subunit for delivery into cells via its receptor. The peptide conjugate was found to inhibit herpes simplex type 1 replication in quiescent Vero cells [8]. Using detailed knowledge of the PCNA-interaction domain of $p21^{WAF1}$ derived from two hybrid screens, a peptide has been designed which effectively block the interaction. This 20-mer bound with sufficient affinity to block SV40 replication. A 20-mer peptide sequence derived from p16 has been found to interact with Cdk4 and Cdk6 and inhibited pRB phosphorylation and cell cycle progression [9]. The authors coupled the specific inhibitor peptide to the 16 residue penetration peptide for efficient nuclear delivery. Peptides have even been shown to function as inhibitors in animal models. For example, a tetrapeptide mimicking the substrate of farnesyl protein transferase has also been shown to block the growth of Ras-dependent tumours in nude mice.

Peptide Mimotopes

Peptides functionally resembling the epitopes (mimotopes) bound by antibodies have been isolated and used as experimental vaccine to induce antibodies which protect against infection as shown for hepatitis B, respiratory syncytial virus, Japanese encephalitis and Streptococcus pneumonia. High affinity antibodies typically bind complex structures formed by the tertiary conformation of an antigen. The peptide mimotopes essentially convert a conformational epitope made from a complete protein into a small peptide. It has advantages when only certain epitopes are desired, e.g. to prevent immunopathology in RSV infection; or in the production of recombinant epitopes where the complete polypeptide may be difficult to fold; or where the entire antigen has undesirable biological properties (Staphylococcal toxins in toxic shock syndrome). In the case of carbohydrate antigens, polypeptides that contain the mimotope can be constructed to convert a T-cell independent antigen into a T-dependent antigen for the production of high affinity antibodies and immunogenicity in young animals including humans. Unlike the carbohydrates, peptide mimotopes can be produced as DNA vaccines.

The possibility of using mimotopes as antigens for cancer immunotherapy has been demonstrated for an adenocarcinoma antigen.

Mimotopes can be used as antigens to diagnose infectious disease by detecting antibody. The possibility has been demonstrated with hepatitis C infection.

Mimotopes representing the antigens recognised by autoantibodies against β-islet tissue in diabetes have been demonstrated and it has been proposed that these could be used to monitor the development of disease (10). Similarly mimotopes have been found for pollen allergens which could be used in the diagnosis of allergic disease. In both these cases it is also possible that the mimotopes could be used for therapy by modulating the immune response or in prophylaxis.

Mimotopes representing transplantation antigens have been demonstrated and thus may be used as tolerogens or blockers to prevent transplantation rejection.

Ligand Interactions or Hormone Receptor Interactions

Peptide mimetics have been used as ligands to affinity purify biologically useful molecules as shown for the purification of the blood clotting protein, von Willebrand factor.

The modification of enzyme activity with peptides mimicking substrates has also been demonstrated. Peptide mimetics can be used as hormones as shown for erythropoietin and can be modified to increase biological activity.

Recombinant Methods for Producing Biological Active Peptides

The use of fragments from specific genes or cDNA to produce peptides containing a biological activity of the polypeptide encoded by the gene or an inhibitor of the activity can sometimes be successful. In other instances the activity can be dependent on the conformation of complete polypeptide and cannot be obtained by these techniques. In many cases the use of random peptide libraries in phage or plasmids to produce a peptide which mimics the biological activity has been successful. This involves the screening of large numbers of clones producing an essentially random array of peptides for a peptide of the desired activity.

The activity is sometimes mediated by a peptide which shows an amino acid sequence homology which could explain its biological activity while in many cases the peptide acts as a mimetic for the conformation of the polypeptide or its ligand and has no sequence homology. Indeed the peptide may be a mimetic of a chemically different molecule such as a carbohydrate. It is also possible to use the combinatorial library approach to screen for inhibitors or mediators of complex functions where there is no information on the molecular interactions required.

The ability to isolate active peptides from random fragment libraries can however be highly variable and problems with low affinity interactions have been reported, particularly for peptides required to represent complex conformations such as discontinuous epitopes bound by many antibodies. There is unpredictability in that, libraries that are a rich source of peptides for one ligand may not contain peptides for others. While the ability to obtain desired peptides should be increased with libraries containing larger random peptides and more random peptides there are practical difficulties in conducting high throughput screening or affinity purification particularly since it has been shown that high-density affinity purification is inefficient. There is also uncertainty about the degree to which peptides isolated from the random peptide libraries will retain their binding or biological activity when produced as part of different delivery strategies such as fusions with different polypeptides. There is thus an opportunity to supplement or improve the existing technology with new strategies.

Biodiverse Peptide Domain Libraries from defined Genomic Sources

Peptides present potential therapeutic and prophylactic agents for many human and animal diseases, biochemical disorders and adverse drug effects, because they can interact with other molecules with high specificity and affinity. However, a major problem to be overcome in the field of peptide therapeutics and prophylactics is the identification of specific amino acid sequences having a desired antagonist or agonist activity against a particular biological activity in a particular cellular environment. Such candidate peptide drugs may be particularly difficult to identify from truly random peptide libraries that lack any enrichment for sequences encoding molecular shapes suitable for binding biological structures. In contrast, nature has already assembled a rich source of such domains within the myriad of peptides, polypeptides and proteins encoded by the diverse range of genomes that make up the biosphere.

A wide range of different methods have been put forward to facilitate the screening of biological libraries (such as cDNA libraries) in an expedient manner to identify suitable protein or polypeptide molecules. Libraries of thousands and in some cases even millions of polypeptides or peptides have been prepared by gene expression systems and displayed on chemical supports or in biological systems suitable for testing biological activity. Generally such libraries are made from either individual genomes of organisms believed to be rich sources of new drugs (such as 'extremophile' bacterial species) or from a mixture of uncharacterised genomes isolated directly from the environment.

While the screening of biodiverse libraries has proven valuable, such libraries tend to be biased towards the frequency with which a particular organism is found in the native environment and may not necessarily represent the true population of the biodiversity found in a particular biological sample. Moreover, such screens are normally intended to isolate genes encoding enzymes, hence attempts are often made to bias such libraries to contain larger inserts which could be expected to encode biologically active enzymes.

In U.S. Pat. No. 5,763,239 in the name of Short et al., a procedure is described for normalising genomic DNA libraries from an environmental sample, in an attempt to address this problem of bias. Because the libraries mentioned in that patent are generated from environmental samples for which little would be known about the genomic constitution of the library the procedure employs complicated normalisation methods to normalise the genomic constitution of the libraries. While that procedure permits some normalisation of the genomes in an environmental sample, the methods that is describes are complicated, there is a risk that rare genomic DNA's will be lost when the methods are applied and/or that new biases will be introduced by the procedure.

In addition to the above, current screening methods often rely on the isolation of genomic nucleic acid sequences using PCR amplification procedures for which little may be known about the genomic sequences. In such cases biases can be introduced through such factors as the presence of disproportional representation of repeated sequences in certain genomes. Furthermore, because no information is known about the genomic constitution of the environmental sample, only limited bioinformatic data can be derived from a screen of the library. This problem is addressed to some extent in U.S. Pat. No. 5,763,239, which seeks to increase the probability that a genomic sequence of low copy number in an environmental sample will have a chance of being represented in a library.

There are, however, currently no available methods for screening normalized biodiverse peptide domain libraries in vivo wherein the entire composition and complexity of the library can be accurately estimated and wherein the screening process provides such comprehensive bioinformatic data useful for rational drug design. Moreover, no methods have been described with are specifically designed for the construction of natural genomic sequence libraries that have been optimised for the expression of domains per se, rather than entire polypeptides. Accordingly, there is a need to develop technologies that provides for the large-scale screening of peptide libraries which are enriched for sequences encoding bioactive domains useful in the determination of useful peptide therapeutics, the basis of which is not necessarily related to the natural role of particular peptide domains.

SUMMARY OF THE INVENTION

Proteins of different function show evidence of evolving by shuffling of domains (eg. nerve growth factor and the low-density liproprotein receptors) or by minor modifications of different residues within conserved domains (serine proteases). The present invention seeks to mimic this evolution by using peptide libraries encoded by known and defined nucleotide sequence fragments that are a rich source of peptides containing amino acid sequences evolved for diverse molecular interactions not necessarily closely related to the function performed within the donor organism. Also described are means of extending the diversity of biodiverse gene fragment libraries further by mutagenesis—either in vivo using PCR amplification under mutagenic conditions, or in vivo by replication of the library in 'mutator' bacterial strains which contain mutations in genes involved in mismatch repair of DNA.

The present invention provides a method for identifying a modulator to mediator of a biological activity, which activity includes antigenicity and or immunogenicity, said method comprising the step of:

(i) producing a gene fragment expression library derived from defined nucleotide sequence fragments; and (ii) assaying the expression library for at least an amino acid sequence derived from step (i) for a biological activity wherein that activity is different from any activity the amino acid sequence may have in its native environment.

It will be appreciated that the present invention has broad reaching application for identifying amino acid sequences that have a novel activity compared to that for which they may be recognised as having in their ordinary natural environment. For example, the present invention is particularly useful for screening genome fragment expression libraries for amino acid sequences reactive with particular antibodies by for example affinity chromatography of a phage display library. Moreover, the present invention provides a mean for defining amino acids essential for modulating a biological activity such as, for example, antibody binding. It also provides a means for isolating amino acid sequence modulators or mediators of a biological activity, which are capable of functioning independently of the artificial constrains of the screening system by which they are identified (e.g. gene fusions etc.).

In particular the present invention is particularly useful for identifying novel therapeutics such as vaccines or immunotherapeutic antigens, antibiotics or inhibitory agents that may serve as candidate agonists and antagonists of any biological activity. For example, biodiverse gene fragment libraries may be used to produce antigens that can be used for vaccines or for immunotherapy of allergic disease or autoimmune disease. In the case of the allergen immunotherapy it is especially desirable to obtain a high affinity peptide (which is rare from random peptide libraries) because it may be used as a monovalent antigen to avoid crosslinking of IgE on mast cells.

This system may also be used in high through-put screening for agents which target specific protien:DNA, peptide: DNA or peptide:protein; protein:protein interactions or a structure such as the cell wall or a membrane transport component.

A distinct advantage of the technology described herein is that through having greater control over the composition of an amino acid sequence expression library by knowing its defined constitution, one can intentionally maximise the phylogenetic distance between the constituent genomes of the library to ensure a maximal degree of diversity which, could in principle rival the sequence diversity of environmentally derived genome samples, notwithstanding the fact that such samples may contain more species diversity per se. This approach will become increasingly powerful as the range of available nucleotide sequences increase further.

In one embodiment there is provided a method for identifying a modulator or mediator of a biological activity, which activity includes antigenicity and/or immunogenicity, said method comprising the steps of:

(i) producing a gene fragment expression library derived from defined nucleotide sequence fragments, which nucleotide sequence encodes at least a sequence of amino acids;

(ii) assaying the expression library for at least an amino acid sequence derived from step (i) for a biological activity wherein the library is adapted to display a range of amino acid sequences each of which may vary by at least an amino acid; and (iii) identifying those amino acids essential for modulating the biological activity, which activity is different from the activity which the sequence is not normally associated in its native environment.

A sequence of amino acids that is particularly effective in modulating or mediating a biological activity (e.g. antigenicity or immunogenicity) can be selected by comparing the observed activity from a series of different amino acid sequences of a similar constitution. Using differences in the observed activity it is possible to identify those amino acids essential for the activity and those which are either desired for the activity or in the alternate case those which are a hindrance to achieving effective activity.

In a second embodiment the method may be employed to identify novel antibacterial peptides that are conditionally released from a fusion protein. According to this embodiment, there is provided a method of identifying an antibacterial peptide, comprising:

(i) transforming or transfecting a first bacterial population of cells with a peptide expression library derived from defined nucleotide sequence fragments;

(ii) growing said first bacterial population for a time and under conditions sufficient for expression of the amino acid sequences encoded within said library to occur and for release of the amino acid sequences from their cognate fusions;

(iii) contacting the expression amino acid sequences with pathogenic bacteria;

(iv) identifying those sequence(s) that are capable of inhibiting the growth of the pathogenic bacteria, or killing the pathogenic bacteria; and (v) selecting those sequences from the identification step in step (iv) that are not associated with the inhibition of growth of the pathogenic bacteria, or killing the pathogenic bacteria in their native environment.

In a third embodiment, there is provided a method for identifying a modifier of a biological activity associated with a hose cell, said method comprising the steps of:

(i) Expressing a reporter molecule operably under the control of the biological activity in the cell, wherein at least a molecule associated with the biological activity comprises an amino acid sequence encoded by a nucleotide sequence that is placed operably in connection with a promoter;

(ii) Incubating at least a cell from step (i) in the presence of an amino acid sequence(s) from a gene fragment expression library derived from a defined genomic sequence, under conditions promoting interaction between the amino acid sequence(s) and a nucleotide or amino acid sequence involved with the biological activity; and (iii) Identifying at least an amino acid sequence that in the presence of the cells is capable of modifying expression of said reporter molecule, or the biological activity; and (iv) Selecting those sequences in step (iii) that are not generally recognised as being able to modifying expression of said reporter molecule, or the biological activity in their native environment.

Preferably the method described in this embodiment is repeated as often as is necessary to ensure that a substantially all of the amino acids encoded by the defined nucleotide sequence are presented to the biological activity.

In a fourth embodiment that is provided a method of identifying an antagonist of a biological activity, said method comprising the steps of:

(i) placing expression of a reporter molecule operably under the control of a biological activity in a cell, wherein at least one partner of said biological activity comprises an amino acid sequence encoded by a nucleotide sequence that is placed operably in connection with a bacterial-expressible promoter in a suitable vector, wherein (a) the nucleotide sequence is derived from a nucleotide sequence of known and sequenced origin and (b) the biological activity is different from any activity that the amino acid sequence may have in its native environment;

(ii) incubating the cell in the presence of a candidate compound to be tested for the ability to antagonise the biological activity; and (iii) selecting cells wherein expression of said reporter molecule, or biological activity, is modified.

Any nucleotide sequence of known nucleotide composition may be used in the present invention. Preferably the nucleotide sequence is derived from a substantially sequenced genome of a microorganism and/or a compact eukaryotic species (ie a species with a high proportion of sequence encoding polypeptide). Most preferably, the nucleotide sequence is derived from a fully sequenced genome from a microorganism and/or a compact genome of a eukaryotic species that is a genome containing a high percentage of DNA encoding polypeptides.

Desirably, the present invention employs a peptide expression library made from defined genomic sequence present either in isolation or in combination with other defined genomic sequence to identify amino acid sequence(s) that may be suitable candidates for rational drug design while at substantially the same time providing comprehensive bioinformatic data about those candidates. The bioinformatic data derived from the method may be used to identify those amino acids important in modulating the biological activity.

In a fifth embodiment there is provided a method for identifying a modulator of a biological activity, said method comprising the steps of:

(i) producing an amino acid expression library derived from a defined genomic sequence;

(ii) contacting an amino acid sequence derived from the expression library with a reporter molecule that is operably under the control of a biological activity associated with a host; and (iii) identifying an amino acid sequence capable of modulating the biological activity wherein that activity is different from any activity the amino acid sequence may have in its native environment.

In a sixth embodiment, there is provided a method for identifying an amino acid sequence that is capable of modulating a biological activity in a host cell, said method comprising the steps of:

(i) producing a library in a host wherein (a) the transformed cells of said library contain at least a first nucleotide sequence that comprises or encodes a reporter molecule the expression of which is operably under control of said biological activity and a second nucleotide sequence derived from a known genomic sequence that is capable of encoding the amino acid sequence when placed operably under the control of a suitable promoter sequence and wherein (b) substantially all of the known genomic sequence is present within the population of transformed cells making up said library and the biological activity is different from any activity the amino acid sequence may have in its native environment;

(ii) culturing said cellular host for a time and/or under conditions sufficient for expression of said second nucleotide sequence to occur; and (iii) selecting or screening for cells wherein expression of said reporter molecule is modified.

Preferably, the method defined by the sixth embodiment also includes the additional steps of:

(iv) comparing the range of amino acid sequences that can be derived from the known genomic sequence against those sequences exhibited biological activity; and (v) determining those amino acids which are essential for modifying the reporter molecular activity.

In a particularly preferred form the invention, a plurality of defined genomic sequences derived from different organisms may be expressed in the gene fragment expression library. Where genomic sequences from more than one organism are used in the method each of the sequences are preferably provided in equal molar amounts to ensure that an equal proportion of the sequences are included in the method.

The complexity of the gene fragment expression library may also be augmented by subjecting the defined genomic sequence(s) derived from those sequences to methods that mis-read or mutate the sequence(s). Alternatively, or in addition, the complexity of the library may also be augmented by expressing the defined genomic sequence in each of its different reading frames. It may also be expressed in its reverse reading frames. Thus, allowing for expression of a gene sequence in each possible reading frame, for any particular sequence there will be six different possible combinations.

The present invention also contemplates amino acid sequences identified by the method of the present invention as well as the use of those molecules in a pharmaceutical composition. The pharmaceutical composition comprising an amino acid sequence capable of modulating or mediating a biological activity or the function of a biological molecule and a pharmaceutically acceptable carrier and/or diluent.

The present invention also provides a vector (or pool of up to 3 vectors) capable of expressing a nucleotide sequence in each of its possible reading frames and wherein each of the amino acid sequences so produced are expressed as a fusion with a second amino acid sequence in which they are conformationally constrained, wherein said vector at least comprises:
  (i) a first expression cassette, comprising:
    (a) a multiple cloning site for insertion of a nucleotide sequence encoding said amino acid sequence, wherein said multiple cloning site may be adjacent to one or more second nucleotide sequences encoding a polypeptide loop such that a fusion polypeptide is capable of being produced between said first and second amino acid sequences;
    (b) a terminator sequence adjacent to the multiple cloning site and distal to said promoter sequence and second nucleotide sequences;
  (ii) a means for expressing the first nucleotide sequence in each of its reading frames;
  (iii) a bacterial origin of replication and/or a bacteriophage origin of replication; and
  (iv) a second expression cassette encoding a bacterial selection marker gene.

Another aspect of the present invention provides for modification of the target microorganism whose growth or alternate function may be inhibited. This microorganism may be modified for screening purposes in a manner that facilitates screening such as by:
  (i) The introduction of novel antibiotic resistance markers by homologous recombination, by transformation of plasmids or by random mutagenesis and selection;
  (ii) The introduction (by homologous recombination or plasmid transformation) of one or more reporter gene/s (eg. luciferase or β-galactosidase) under the control of an endogenous promoter associated with pathology or virulence. For example, the promoters for the RNAIII or RAP genes of *Staphylococcus aureus* could be used to control expression of a reporter gene that could be easily detected. Such methods are well known to those skilled in the art—see international (PCT) patent WO 90/40979, for example.

The present invention also provides a means of exploiting bioinformatic data concerning homologous sequences encoding structural domains in sequenced genomes, to design defines libraries by such techniques as degenerate PCR techniques or chemical DNA synthesis that focus on a particular affinity domain. The diversity of such a library may be further increased by mutagenesis techniques known to those skilled in the art.

The present invention are provides a high through-put screening technique for the identification of clones (from the library) that produce amino acid sequences capable of inhibiting growth or repressing virulence genes of the pathogenic target organism.

DETAILED DESCRIPTION OF THE PREFERRED EMBODIMENTS

The screening methods described herein differ from existing rational design approaches that attempt to model candidate therapeutic peptides based on homologies in the databases to natural inhibitory peptides. The existing approaches focus on amino acid sequences that have previously been identified from their natural source due to their inhibitory properties. In contrast, the method described herein, empirically determine amino acid sequences, that may modulate a biological activity, from a wide array of candidates encoded in a genomic expression library derived from nucleotide sequences which have been completely determined without regard for their original function of those sequences in nature.

Natural biologically interactive peptide and polypeptide domains are thought to have evolved by selection from a bank of available domains in each organism in which they arose. Within any organism there is a tremendous amount of diverse coding information. To harness this diversity a genetic screen has been derived which maximises the diversity of a pool of potential biologically interactive domains. Moreover, since the information used in the screen is derived from sequenced genetic information, structural information that has already evolved in nature may be exploited by comparing biologically interactive molecules against similar sequences from a sequence and test nucleotide sequence. This information desirably permits the identification of particular amino acids that are essential to the binding action of the biological activity and/or possibly particular motifs that are essential to or at least implicated in the binding reaction. Thus, the present invention provides screening methods for identifying potential amino acid sequence(s) that are capable of modulating or mediating biological activities involving peptides, oligopeptides, proteins and or nucleic acid sequences.

Therefore, the present invention resides in a method for identifying a modulator or mediator of a biological activity, which activity includes antigenicity and or immunogenicity, said method comprising the step of:
  (i) producing a gene fragment expression library derived from defined nucleotide sequence fragments; and
  (ii) assaying the expression library for at least an amino acid sequence derived from step (i) for a biological activity wherein that activity is different from an activity the amino acid sequence may have in its native environment.

As used herein, the term "biological activity" shall be taken to include biological interactions leading to a physical association between two or more molecules or "partners". Such activity should be interpreted in its broadest context and include, for example, interactions such as peptide:peptide peptide:protein, protein:protein, antigen:antibody, peptide:nucleoic acid sequence, protein:nucleic acid sequence, peptide:ligand and protein:ligand. For example, the activity includes but is not limited to any interaction that modulates or mediates antibody binding or antigen binding or any other amino acid sequence based interaction described in the background section of this specification. Preferably, the physical association involves a cellular process or alternatively, is required for a cellular event to occur and wherein that activity is different from any activity the amino acid sequence may have in its native environment. In addition, it shall include activity that leads to the disruption of a biological structure and/or activity. The "physical association" may involve the formation of an induced magnetic field or paramagnetic field, covalent bond formation such as a disulfide bridge formation between polypeptide molecules, an ionic interaction such as occur in an ionic lattice, a hydrogen bond or alternatively, a van der Waals interaction such as a dipole-dipole interaction, dipole-induced-dipole interaction, induced-dipole-induced-dipole interaction or a repulsive interaction or any combination of the above forces of attraction.

Fragments from any nucleotide sequence of a known nucleotide composition may be used in the present invention. Those skilled in the art will be aware of a variety of methods for producing nucleotide sequence fragments including: mechanical shearing (eg, by sonication), Digestion with a nuclease (eg, by DnaseI), digestion with restriction enzyme/s, polymerase chain reaction using degenerate primers. Preferably the nucleotide sequence is derived from a substantially sequenced genome of a microorganism and/ or a compact eukaryotic species. More preferably, the nucleotide sequence is derived from a fully sequenced genome from a microorganism and/or a compact eukaryotic species. Most preferably a plurality of different nucleotide sequences are expressed in the gene fragment expression libraries which sequences are derived from biodiverse organisms. Thus, biodiverse nucleotide sequences are desirably employed in the method of the invention to prepare the expression libraries. Where sequenced genomes or fragments thereof from different organisms are used in the method each of the genomes or fragments thereof should be provided in equal molar amounts to ensure that an equal proportion of sequenced genomes or fragments thereof are included in the method.

Those working in the field will appreciate that gene fragment expression library may be prepared using any expression vector known in the art. Preferably the vectors, selected for use in the library possess strong promoters therein enhancing amino acid sequence expression. For example, in a bacterial system bacterial-expressible promoters that may be used in the vector may include, but would not be limited to, pT7-Select, pET, pZero, pHook, pTYB or a derivative thereof. Other vectors that may be used in the vector are discussed in more detail below.

The amino acid sequence(s) derived from the gene fragment expression library may be expressed in a conformationally constrained or conformationally unconstrained form. Amino acid sequences that are expressed in a conformationally constrained form may be expressed within a second polypeptide as a fusion protein such that they are effectively "nested" in the secondary structure of the second polypeptide. Alternatively, the amino acid sequence(s) may be circularised by means of oxidising flanking cysteine residues to limit conformational diversity. This may be particularly beneficial where the amino acid sequence(s) are nested within a surface-exposed or functional site of a protein, such that they are accessible to the biological activity of interest. For example, the amino acid sequence(s) may be expressed within a thioredoxin (Trx) polypeptide loop. Whilst not being bound by any theory or mode of action, expression of the amino acid sequence(s) in a conformationally constrained form limits the degrees of freedom and the entropic cost associated with its binding, imparting a high degree of affinity and specificity to the interaction.

Those working in the field will appreciate that the present invention has broad reaching application. By way of exemplification the present invention is particularly useful for screening gene fragment expression libraries for amino acid sequence(s) reactive with particular antibodies by for example affinity chromatography of a phage display library. Alternatively, biodiverse gene fragment libraries may be used to identify antigenic or immunogenic sequences that may be used for vaccines or for immunotherapy of allergic disease or autoimmune disease.

In one embodiment there is provided a method for identifying a modulator or mediator of a biological activity, which activity includes antigenicity and or immunogenicity, said method comprising the steps of:

(i) producing a gene fragment expression library derived from defined nucleotide sequence fragments, which nucleotide sequence encodes at least a sequence of amino acids;

(ii) assaying the expression library for at least an amino acid sequence derived from step (i) for a biological activity wherein the library is adapted to display a range of amino acid sequences each of which may vary by at least an amino acid; and (iii) identifying those amino acids essential for modulating the biological activity, which activity is different from the activity which the sequence is not normally associated in its native environment.

A sequence of amino acid that is particularly affective in modulating biological activity can be selected by comparing the observed biological activity from a series of different amino acid sequences of a similar constitution. Using differences in the observed biological activity it is possible to identify those amino acids essential for biological activity and those which are either desired for the activity or in the alternate case those which are a hindrance to achieving effective activity.

The present invention has broad reaching application for identifying amino acid sequences that have a novel activity compared to that for which they may be recognised as having in their ordinary natural environment.

In a particularly preferred for of this embodiment there is provided a method for identifying an amino acid sequence which has either antigenic or immunogenic activity, said method comprising the steps of:

(i) producing a gene fragment expression library derived from defined nucleotide sequence fragments, which nucleotide sequence encodes at least a sequence of amino acids;

(ii) assaying the expression library for at least an amino acid sequence derived from step (i) for a antigenic or immunogenic activity wherein the library is adapted to display a range of amino acid sequences each of which may vary by at least an amino acid;

(iii) identifying those amino acid sequences essential for modulating or mediating the antigenic or immunogenic activity; and (iv) selecting those sequences from the identification step in step (iii) that are not associated the antigenic or immunogenic activity in their native environment.

Preferably the gene fragment libraries employed in this embodiment of the invention are used to identify or produce antigens that can be used for vaccines or for immunotherapy of allergic disease or autoimmune disease. In the case of the allergen immunotherapy it is especially desirable that high affinity peptides are identified (which are rare from random peptide libraries) because they may be used as monovalent antigens to avoid specific crosslinking immunological reactions such as crosslinking of IgE on most cells.

In a second embodiment the peptide libraries of the present invention may be employed to identify novel antibacterial amino acid sequences that are conditionally released from a fusion protein. According to this embodiment, there is provided a method of identifying a antibacterial amino acid sequence, comprising:
(i) transforming or transfecting a first bacterial population of cells with a peptide expression library derived from defined nucleotide sequence fragments;
(ii) growing said first bacterial population for a time and under conditions sufficient for expression of the amino acid sequences encoded within said library to occur and for release of the amino acid sequences from their cognate fusions;
(iii) contacting the expressed amino acid sequences with pathogenic bacteria;
(iv) identifying those sequence(s) that are capable of inhibiting the growth of the pathogenic bacteria, or killing the pathogenic bacteria; and
(v) selecting those sequences from the identification step in step (iv) that are not associated with the inhibition of growth of the pathogenic bacteria, or killing the pathogenic bacteria in their native environment.

It should be appreciated that the method described in this embodiment has broad reaching application for identifying novel amino acid sequences that are capable of inhibiting the growth of pathogenic bacteria, or killing pathogenic bacteria.

In a highly preferred form of this embodiment nucleotide sequences encoding peptide(s) or peptide fusions are inserted within the cloning site of a T7-Select phase vector (Invitrogen) with or without the introduction of a conditional protein cleavage site (such as the temperature sensitive protein splicing element 'intein' modified from the element found in the *Saccharomyces cerevisiae* VMA1 gene (e.g. IMPACT T7 system, New England Biolabs)) cloned into the fusion junction of the vector. The first bacterial population is then grown for a time and under conditions sufficient for expression of the peptides encoded by said library to occur. In cases where conditional cleavage of the peptide from its fusion context is desired (e.g., the intein system), the bacterial/phase population may be put under conditions where cleavage can occur (e.g. low temperature in the case of the intein mutant cleavage)). The individual clones or pools of clones in said library are then separated into replica arrays. At least one of said replicated arrays is then lysed to produce a lysate array. Note this is not necessary in the case of lytic phase vectors such as T7-select. The lysate array is then brought into physical relation with pathogenic bacteria. Those lysates that are capable of inhibiting the growth of the pathogenic bacteria, or killing the pathogenic bacteria can then be identified by standard techniques.

For convenience, the pathogenic bacterium described in this embodiment may be contained within a bacterial lawn on solid media, however this is not essential to the performance of this embodiment.

Preferably, the subject method further comprises the step of keying the lysate back to the replicated array to localise the bacterial cell that expresses the same antibacterial peptide as that expressed in said lysate. More preferably, the genetic sequence encoding the peptide is isolated for the purposes of producing the antibacterial peptide encoded therefor.

In an exemplification of this embodiment, *Escherichia coli* BL21 lysates containing protein expressed from pET peptide libraries, are assayed for their ability to inhibit the growth of pathogenic microorganisms or alternatively, for their ability to kill pathogenic microorganisms, wherein individual clones derived from a population of cells transformed or transfected with the subject peptide library are either replica-plated onto semi-permeable membranes, such as nitrocellulose or nylon membranes, or alternatively, replica-picked, to cultures and cultures in which expression of the cloned peptide sequence is to be induced, prior to lysis. Replica-plating and/or replica-picking can be performed manually or with the assistance of robotics. Samples comprising those colonies in which expression is to be induced are lysed, for example by exposure to chloroform or by infection with a bacteriophage such as T7 bacteriophage, and overlayed on a freshly seeded lawn of pathogenic bacteria.

In the case of lytic phage libraries (such as those made in the T7-select system), a double-faced petri-dish can be used. In this case a phage overlay occupies one face of the dishes that is separated from the other faces by a supported semi-permeable membrane (made of a material such as nitrocellulose or nylon) on which a seeded lawn of the pathogenic bacteria lies. Thus the semi-permeable membrane separates the phage overlay from the pathogenic bacteria that can be grown on different media respectively (see example).

The ability of individual peptide-expressing clones to inhibit growth or to kill the pathogenic bacterium in question is assayed by detecting the presence of a 'plaque-like' "clearing" or "hole" in the lawn of pathogenic bacteria directly beneath the position where the lysate containing the expressed antibacterial peptide occurs.

Those skilled in the art will recognise that this method provides an opportunity of isolating a phage or plasmid clone expressing the activity that gave rise to the corresponding hole in the lawn on the opposite.

In a third embodiment, there is provided a method for identifying a modifier of a biological activity associated with a host cell, said method comprising the steps of:
(i) Expressing a reporter molecule operably under the control of the biological activity in the cell, wherein at least a molecule associated with the biological activity comprises an amino acid sequence encoded by a nucleotide sequence that is placed operably in connection with a promoter;
(ii) Incubating at least a cell from step (i) in the presence of an amino acid sequence(s) from a gene fragment expression library derived from a defined genomic sequence, under conditions promoting interaction between the amino acid sequence(s) and a nucleotide or amino acid sequence involved with the biological activity;
(iii) Identifying at least an amino acid sequence that in the presence of the cells is capable of modifying expression of said reporter molecule, or the biological activity; and
(vii) Selecting those sequences in step (iii) that are not generally recognised as being able to modifying expression of said reporter molecule, or the biological activity in their native environment.

Preferably the method is repeated as often as is necessary to ensure that a substantially all of the amino acids encoded by the defined nucleotide sequence are presented to the biological activity.

In a particularly preferred form of the third embodiment the gene fragment expression library is prepared in a pET vector. Such as those that are commercially available from Novagen. pET vectors as described herein are particularly useful in such applications, by virtue of the strong T7 promoter sequence contained therein which facilitates bacterial expression in strains expressing T7 polymerase. Those skilled in the art will appreciate that other bacterial expression vectors will be equally applicable.

In a highly preferred form of this embodiment, a nucleotide sequence(s) derived from a defined genetic sequence is incorporated into a pET vector such that the nucleotide sequence is operably linked to an appropriate bacterial translation initiation sequence as described supra. A second nucleotide sequence may further be expressed in association with the first nucleotide sequence such that the resultant peptide is constrained within the active site loop of thioredoxin or within oxidised flanking cysteine residues. As with other embodiments of the invention, the second nucleotide sequence may be synthetic and/or derived from genomic sources.

Expression from the pET vector is achieved by infection of bacteria which contain the library plasmid with bacteriophage T7 or alternatively, by using publicly available strains such as E. coli BL21, which contain the T7 polymerase gene under lac control, because in such strains IPTG may be added to growth media to induce expression of the T7 polymerase gene. Derivatives of the strain BL21 (such as strain Bl21trxB (DE3), which contain a mutation in the thioredoxin reductase gene trxB, are particularly useful for ensuring that disulphide bonds remain oxidised in the bacterial cytoplasm.

This embodiment is particularly useful for identifying antagonists of a biological activity. In such situations, the undesirable biological activity is preferably functional in the absence of the drug being screened and perturbation of that interaction is assayed in the presence of a candidate drug compound, wherein modified reporter gene expression is detected in the manner described for other embodiments of the invention.

Preferably, where the reporter molecule is lethal to the bacterial cell, expression thereof should not occur until the amino acid sequence(s) candidate compound is provided to the cell for a time and under conditions sufficient to antagonise the biological activity leading to reporter expression. Accordingly, in a preferred from this embodiment provides a method of identifying an antagonist of a biological activity in a bacterial cell, comprising the steps of:

(i) placing the expression of a cytostatic or cytotoxic reporter molecule operably under the control of a biological activity in said cell, wherein at least one binding partner in said biological activity comprises an amino acid sequence encoded by a nucleotide sequence that is placed operably in connection with a bacterially-expressible promoter;

(ii) incubating the cell in the presence of at least an amino acid sequence candidate compound to be tested for its ability to antagonise the biological activity for a time and under conditions sufficient for antagonism to occur, wherein the amino acid sequence candidate compound is derived from a gene fragment expression library derived from a defined genomic sequence;

(iii) expressing the binding partner under the control of the bacterially expressible promoter for a time and under conditions sufficient to result in expression of the reporter molecule in the absence of antagonism; and (iv) selecting surviving or growing cells.

Preferably, the inducible bacterially-expressible promoter is the T7 promoter. In such circumstances, the expression of the reporter molecule may be induced by infecting cells with bacteriophage T7, which supplies the T7 polymerase function. Alternatively, the bacterial cell may be a cell that contains the T7 polymerase under lac control (e.g. E. coli BL21 cells), in which case the promoter may be induced by the addition of IPTG to growth medium. The candidate compound may be any small molecule, drug, antibiotic or other compound, the only requirement being that it is capable of permeating or being actively taken up by the bacterial cell or alternatively, is modified by the addition of a carrier molecule to facilitate such uptake.

In a fourth embodiment there is provided a method of identifying an antagonist of a biological activity, said method comprising the steps of:

(i) placing expression of a reporter molecule operably under the control of a biological activity in a cell, wherein at least one partner of said biological activity comprises an amino acid sequence encoded by a nucleotide sequence that is placed operably in connection with a bacterial-expressible promoter in a suitable vector, wherein (a) the nucleotide sequence is derived from a nucleotide sequence of known and sequenced origin and (b) the biological activity is different from any activity that the amino acid sequence may have in its native environment;

(ii) incubating the cell in the presence of a candidate compound to be tested for the ability to antagonise the biological activity; and (iii) selecting cells wherein expression of said reporter molecule, or biological activity, is modified.

This method is particularly useful for identifying novel drugs such as antibiotics or inhibitory agents that may serve as candidate agonists and antagonists of any biological activity. Moreover this system may be used in high throughput screening for novel antibiotics or other inhibitory agents which target specific amino acid sequence:nucleic acid sequence interactions or amino acid sequence:amino acid sequence interactions.

Preferably, where the reporter molecule is lethal to the bacterial cell, expression thereof should not be allowed until the candidate compound is provided to the cell for a time and under conditions sufficient to antagonise the biological activity leading to reporter expression. Accordingly, a preferred aspect of this embodiment provides a method of identifying an antagonist of a biological activity in a bacterial cell, comprising:

(i) placing the expression of a cytostatic or cytotoxic reporter molecule operably under the control of a biological activity in said cell, wherein at least one binding partner in said biological activity comprises an amino acid sequence encoded by a nucleotide sequence that is placed operably in connection with a bacterially-expressible promoter, wherein (a) the nucleotide sequence is defined and is derived from a nucleotide sequence of known origin and (b) the biological activity is different from any activity the amino acid sequence may have in its native environment;

(ii) incubating the cell in the presence of a candidate compound to be tested for its ability to antagonise the biological activity for a time and under conditions sufficient for antagonism to occur;

(iii) expressing of the binding partner under the control of the bacterially expressible promoter for a time and under conditions sufficient to result in expression of the reporter molecule in the absence of antagonism; and (iv) selecting surviving or growing cells.

In a highly preferred example of this embodiment, the inducible bacterially expressible promoter is the T7 promoter. A person skilled the field will observe that any other bacterial inducible promoter may be used in the invention. This embodiment is only being exemplified in relation to the promoter for convenience. In such circumstances, the expression of the reporter molecule may be induced by infecting cells with bacteriophage T7, which supplies the T7 polymerase function. Alternatively, the bacterial cell may be a cell which contains the T7 polymerase under lac control (e.g. *E. coli* B121 cells), in which case the promoter may be induced by the addition of IPTG to growth medium. The candidate compound may be any small molecule, drug, antibiotic or other compound, the only requirement being that it is capable of permeating or being actively taken up by the bacterial cell or alternatively, is modified by the addition of a carrier molecule for facilitate such uptake.

Desirably, the present invention employs a gene fragment expression library made from defined genomic sequence present either in isolation or in combination with other defined genomic sequence to identify amino acid sequence(s) that may be suitable candidates for rational drug design while at substantially the same time providing comprehensive bioinformatic data about those candidates. The bioinformatic data derived from the method may be used to identify those amino acids important in modulating the biological activity.

Using knowledge of the phylogenetic relationship between microorganisms, a mixture of particular genomes can be designed to maximise the sequence diversity in the peptide expression library. This approach has several distinct advantages over cloning and expressing DNA purified directly from the environment. First, the true diversity and bias of the library can be more easily approximated. Hence measures can be implemented to maximise the domain diversity and to minimise bias towards the genomes of dominant species. Second, artificially pooling DNA derived from distinct known organisms allows unique opportunities to survey diverse genomes that may not occur together in nature. For example, the genomes of certain archaebacteria could be simultaneously screened with those of obligate parasites such as mycoplasmas and/or diverse gram positive and/or gram negative organisms. Third, the alignment of sequences derived from a screen can be used to reveal consensus motifs. Moreover, other potential related motifs can be excluded as potential drug candidates if they are not identified from any of the genomes in which they theoretically occur, despite exhaustive screening at a complexity that would be predicted to cover all of the potential domains encoded by the genome/s yet failed to exhibit the required activity. This information can be used to design optimal peptides that mimic the consensus motifs identified in the biological screen while lacking alternative residues of structurally related peptides that were presumably included in the exhaustive screen. Finally, using the pooled genomes of sequenced organisms facilitates certain powerful bioinformatic analyses that may be useful in the design of therapeutic peptides.

In a fifth embodiment there is provided a method for identifying a modulator of a biological activity, said method comprising the steps of:
(i) producing an gene fragment expression library derived from a defined genomic sequence; (ii) contacting an amino acid sequence derived from the expression library with a reporter molecule that is operably under the control of a biological activity associated with a host; and
(iii) identifying an amino acid sequence capable of modulating the biological activity wherein that activity is different from any activity the amino acid sequence may have in its native environment.

Preferably, at least one of the partners in the biological activity contemplated by this embodiment is a peptide, polypeptide, protein or enzyme molecule or a derivative thereof. According to this embodiment, the remaining partner(s) is (are) a molecule selected from the list comprising nucleic acid such as single-stranded or double-stranded RNA or DNA, a peptide, polypeptide, protein, enzyme, carbohydrate, amino acid, nucleotide, nucleoside, lipid, lipoprotein, vitamin, co-enzyme, receptor molecule, hormone, chemical compound, cyclic AMP, metal ion or second messenger molecule, amongst others. More preferably, the biological activity is a protein:protein interaction or a protein:peptide interaction or a protein:polypeptide interaction.

In a particularly preferred form, the biological activity is between a first partner comprising an amino acid sequence and a second partner, comprising a nucleic acid molecule such as DNA or RNA or alternatively, an amino acid sequence or a derivative or analogue thereof.

According to a sixth embodiment, there is provided a method for identifying an amino acid sequence that is capable of modulating a biological activity in a host cell, said method comprising the steps of:
(i) producing a library in a host wherein (a) the transformed cells of said library contain at least a first nucleotide sequence that comprises or encodes a reporter molecule the expression of which is operably under control of said biological activity and a second nucleotide sequence derived from a known genomic sequence that is capable of encoding the amino acid sequence when placed operably under the control of a suitable promoter sequence and wherein (b) substantially all of the known genomic sequence is present within the population of transformed cells making up said library and the biological activity is different from any activity the amino acid sequence may have in its native environment;
(ii) culturing said cellular host for a time and/or under conditions sufficient for expression of said second nucleotide sequence to occur; and
(iii) selecting or screening for cells wherein expression of said reporter molecule is modified.

The second nucleotide sequence used in the method may be derived from any known genomic sequence. By using a sufficient number of second nucleotide species to ensure that the entire sequence of the known genomic sequence is assayed bioinformatic data can be gathered from sequences which not only gave a positive result in the test system but also those sequences which failed to react. By comparing reactive amino acid sequences against similar sequences in a genome that either caused a reaction or alternatively failed to cause a reaction, sequence motifs as well as individual amino acids can be identified that may be implicated in a biological activity. In addition, if the screen is sufficiently comprehensive to ensure adequate coverage, certain alternative residues/motifs represented in the library can be shown to be suboptimal if incorporated into the design of inhibitors of the activity.

Thus, in a preferred form this embodiment provides a method of identifying a amino acid sequence(s) that is capable of modulating a biological activity in a host said method comprising the steps of:
(i) producing a peptide library in a host wherein (a) the transformed cells of said library contain at least a first nucleotide sequence which comprises or encodes a reporter molecule the expression of which is operably under control of said biological activity and a second nucleotide sequence derived from a known genomic sequence which is capable of encoding said amino acid sequence(s) when placed operably under the control of a suitable promoter sequence and wherein (b) substantially all of the known genomic sequence is present within the population of transformed cells making up said library.

(ii) culturing said cellular host for a time and/or under conditions sufficient for expression of said second nucleotide sequence to occur;
(iii) selecting or screening for cells wherein expression of said reporter molecule is modified;
(iv) comparing the range of amino acid sequences that can be derived from the known genomic sequence against those sequences which modulated biological activity; and
(v) determining those amino acids which are essential for modifying the reporter molecule activity.

In another embodiment the present invention therefore provides a vector capable of expressing a nucleotide sequence in each of its possible reading frames and wherein each of the amino acid sequences so produced are expressed as a fusion with a second amino acid sequence in which they may be conformationally constrained, wherein said vector at least comprises:
(i) a first expression cassette, comprising;
  (a) a multiple cloning site for insertion of a first nucleotide sequence encoding said first amino acid sequence, wherein said multiple cloning site may be adjacent to one or more second nucleotide sequences encoding a polypeptide loop such that a fusion polypeptide is capable being produced between said first and second amino acid sequences;
  (b) a terminator sequence adjacent to the multiple cloning site and distal to said promoter sequence and second nucleotide sequences;
(ii) a means for expressing the first nucleotide sequence in each of its reading frames;
(iii) a bacterial origin of replication and/or a bacteriophage origin of replication; and
(iv) a second expression cassette encoding a bacterial selection marker gene.

In an alternative embodiment, the expression vector of the invention further comprises a second expression cassette comprising a selectable marker gene operably linked to two or more promoter sequences and placed upstream of a terminator sequence, wherein one of said promoter sequences is a bacterially-expressible promoter and wherein one of said promoter sequences is a yeast-expressible promoter.

In another alternative embodiment, the subject vector is further modified to provide for the inducible extracellular expression by means of signal peptide fusions and/or conditional lysis systems. Conditional lysis may be achieved by expression of an inducible lytic gene in bacterial cells, by introducing such sequences into an expression cassette between an inducible bacterial promoter (such as the lac, tac or them more tightly regulated araBAD promoters) and a transcriptional termination sequence, in tandem array with the promoter and terminator sequences already present in the subject expression cassettes.

In a still further embodiment, the conditional lysis of bacteria expressing the said peptide/polypeptide, is brought about by alternative means such as by infection with a suitable bacteriophage or by exposure to appropriate chemical agents such as chloroform and/or SDS. In a particularly preferred form of the invention the vector also includes a third expression cassette allowing conditional expression of a lytic gene (such as those genes produced by bacteriophages).

The present invention also contemplates amino acid sequence(s) identified by the method of the present invention as well as use of those molecules in a pharmaceutical composition. The pharmaceutical composition comprising an amino acid sequence(s) capable of modulating a biological activity or the function of a biological molecule and a pharmaceutically acceptable carrier and/or diluent.

Biodiverse Nucleotide Sequence Fragments

Where sequenced genomes from different organisms are used in the above embodiments each of the genomes should be provided in equal molar amounts to ensure that an equal proportion of sequenced genomes are included in the method. Because the genomes are a known size, standard normalisation methods can be applied to ensure that the concentration of one organism's genome is not proportionally greater than that of another organism's genome. Such methods for equalising genomic concentrations are well known to those skilled in the art and include, by way of example, the contribution of proportionately more DNA to the pool from the genomes which are larger, to compensate for the tendency for fragments from such genomes to be under represented if an equal mass of DNA from each genome is combined. In addition, normalisation by other means known to those skilled in the art such as disclosed in U.S. Pat. No. 5,763,239 is contemplated by the present invention.

The present invention attempts to accelerate the evolutionary process by artificially combining domains from different genomes that would have been unlikely to co-evolve. Preferably, the genomic expression libraries are prepared from evolutionary diverse organisms. For example, the organisms could be either derived from: compact eukaryotic genomes such as *Fugu rubripes, Caenorhabditis elegans, Saccharomyces cerevisiae;* and or from prokaryotic microorganisms that have been characterised genetically such as, *E. coli, Aquifex aelitcus, Methanococcus jannaschii, Bacillus subtilis, Haemophilus influenzae, Helicobacter pylori, Neisseria meningiditis, Synechocystis sp Bordetella pertussis, Pasteurella multocida, Pseudomonas aeruginosa, Borrelia burgdorferi, Methanobacterium thermoautotrophicum, Mycoplasma pneumoniae, Archaeoglobus fulgidis* and *Vibrio harveyi.* Those skilled in the art are aware that the number of sequence genomes is increasing rapidly. Compilations of sequenced genomes can be readily obtained by reference to the World Wide Web. For example, a database selected from the following group can be used:

1. the database of The Institute of Genomic Research (TIGR), Rockville, Md. 20850, USA;
2. the database of the Wellcome Trust Sanger Institute, Wellcome Trust Genome Campus, Hinxton, Cambs CB10 1SA, United Kingdom;
3. the Magpie database of Genome Sequencing Projects (Terry Gaasterland, USA; Siv Andersson, Sweden; and Christoph Sensen, Canada);
4. the database of the National Center for Genome Resources (NCGR), Santa Fe, N.M. USA;
5. the database of Genome Sizes (DOGS) of the Center for Biological Sequence Analysis (CBS) of the Technical University of Denmark, Kemitorvet, Building 208, DK-2800, Lyngby, Denmark; and
6. the Genomes On Line Data base (GOLD) of the Ribosomal Database Project (geta-life) of the University of Illinois of Urbana-Champaign, Dept. of Microbiology, Ill., USA.

[(eg see the following URLs for details:
   http://www.tigr.org/tdb/mdb/html
   http:www.sanger.ac.uk
   http://www.genome.ad.jp/kegg/java/org_proj.html
   http://www-fp.mcs.anl.gov/~gaasterland/genomes.html
   http://www.ncgr.org/ http://www.cbs.dtu.dk/databases/DOGS/index.html
http:geta.life.uiuc.edu/~nikos/genomes.html and that the] The method described here are applicable to any subset of the entire pool of sequenced genomes.

The defined nucleotide sequence from which the known nucleotide sequence is derived is not limited only to those sequences that encode amino acids in naturally derived proteins, but also include non-coding nucleotide sequences. Thus, it should be understood that the second nucleotide sequence may be derived from a 5' UTR, an intron (where applicable), a 3' UTR, or alternative reading frames/orientations of the cloned fragment.

Diversity within a pool of sequenced nucleotide sequences may also be expanded by subjecting the sequences to methods that mis-read or mutate those fragments. Thus, in an embodiment of the invention the method may also include a step of artificially mutating the domain libraries. Such methods are well known in the art.

One ways to achieve this end would involve mutation of the known genomic sequence prior to insertion into an expression vector. Thus, in one preferred form, the method of the invention might include the step of: subjecting the known nucleotide sequence to mutagenesis prior to insertion into the expression vector. This may be achieved for example by amplifying the sequenced genomes using mutagenic PCR procedures such as those that include the step of performing the PCR reaction in the presence of manganese. It has been calculated with an error rate of 0.5 bases per 100 bp/cycle that eight mutagenic cycles will produce base changes in 90% of the PCR products and almost 50% will have 2 or 3 substitutions.

Another way in which the domain libraries might be mutated would be through expression of nucleotide fragments in cells that are modified to mutate sequence information. Such strains are deficient in certain enzymes making their mutation rate approximately 5,000 to 10,000 times higher than in the wild-type parent. Thus, the method may include the step of: expressing the biodiverse gene fragments in one or more cell lines that are deficient in at least a DNA repair enzyme. For example, one constructed, the plasmid library can be amplified in bacterial strains deficient in mismatch repair (e.g. strains containing the mutS, mutD and/or mutT mutation), resulting in the generation of mutations. In one exemplification of this embodiment, peptide libraries derived from the expression of genomic DNA are amplified or propagated in bacterial strains which are defective in the epsilon ($\epsilon$) subunit of DNA polymerase III (i.e. dnaQ and mutD alleles) and/or are defective in mismatch repair. *Escherichia coli* mutator strains possessing the mutY and/or mutM and/or mutD and/or mutT and/or mutA and/or mutC and/or mutS alleles are particularly useful for such applications. Bacterial strains carrying such mutations are readily available to those skilled in the art.

Where fragments are mutated prior to generation of an expression library both mutated and unmutated fragments should preferably be combined in the same preparation and are preferably expressed using vectors described herein. The mutated and unmutated libraries will undergo the same selection procedures. The specificity and biological activity of the peptides should then be compared and examined.

To enhance diversity within the sequenced genomic peptide library the fragmented sequenced genomes may also be expressed in each of their different reading frames. Expression of such sequences in this manner may be achieved by any method known in the art including for example by ligating the fragments to adaptors and/or linkers in the three different reading frames or by placing the fragments under the control of internal ribosome entry site/s (IRES) and/or sequences conferring transcriptional/translational slippage. If adaptors are used, a single vector may contain each of the different adaptors or each adaptor may be provided in a different vector.

The fragments may also be expressed in the reverse reading frames. Thus, allowing for expression of a gene sequence in each possible reading frame, for any particular peptide sequence there will be six different possible combinations.

The presence of clones in all reading frames allows the simultaneous screening of random peptides expressed in reading frames that do not occur in nature, together with a variety of natural peptide domains cloned in the appropriate reading frame. This allows a comparison of the relative success of isolation inhibitors from natural peptide libraries as opposed to random peptides libraries. The screening methods described herein are also applicable to the screening of libraries of constained or unconstrained random peptides derived from artificial, non-biological sources.

Definitions

As used here in the phrase "not normally associated in its native environment" shall refer to an activity that the amino acid sequence is not typically associated with. Further, as used herein "native environment" shall be understood to refer to the biological environment in with the amino acid sequence is typically found in nature.

As used herein, the term 'domain' shall be taken to mean a functional unit of an amino acid sequence(s) possessing activity in isolation or in an artificial context and does not necessarily imply any structural features.

As used herein 'amino acid sequence' shall include peptides, oligopeptides and polypeptides including derivatives and analogues thereof being comprised of a number of residues ranging from 1 to 500.

As used herein, the term 'aptamer' shall be taken to include the highly specific, normally conformationally constrained peptides related to the class described by Brent and colleagues (3).

As used herein, the term 'activity' shall be taken to include any enzymatic activity, structural or conformational change occurring outside or inside the cell.

As used herein, the term 'gene fragment expression library' shall be taken to include any expression libraries made using inserts derived from genomic fragments or PCR products of a range of distinct prokaryotic genomes and/or compact eukaryotic genomes.

As used herein the term "derivative" shall be taken to refer to mutants, parts or fragments of a complete polypeptide as defined herein which are functionally equivalent. Derivatives include modified peptides in which ligands are attached to one or more of the amino acid residues contained therein, such as functional groups, carbohydrates, enzymes, proteins, polypeptides or reporter molecules such as radionuclides or fluorescent compounds. Glycosylated, fluorescent, acylated or alkylated forms of the subject peptides are also contemplated by the present invention. Procedures for derivatizing proteins and peptides are well known in the art.

"Analogues" of a peptide, protein, polypeptide or enzymes are functionally equivalent molecules that comprise one or more non-naturally occurring amino acid analogues known to those skilled in the art.

The terms "host" and "cellular host" or similar term refer to prokaryotic and eukaryotic cells capable of supporting the expression of a reporter molecule under the control of a biological activity, irrespective of whether or not the biological activity or the reporter molecule is endogenous to the cell.

Those skilled in the art will be aware that a "transformed cell" is a cell into which exogenous nucleic acid has been introduced, wherein the exogenous nucleic acid is either integrated into the host cell genome or alternatively, maintained therein as an extra chromosomal genetic element such as a plasmid, episome or artificial chromosome, amongst others.

The transformed cell of the present invention may be any cell capable of supporting the expression of exogenous DNA, such as a bacterial cell, insect cell, yeast cell, mammalian cell or plant cell. In a particularly preferred embodiment of the invention, the cell is a bacterial cell, mammalian cell or a yeast cell. In a particularly preferred embodiment of the invention, the cell is a yeast cell.

The term "expression" refers at least to the transcription of a nucleotide sequence to produce an RNA molecule. The term "expression" may also refer to the combined transcription and translation of a nucleotide sequence to produce a peptide, polypeptide, protein or enzyme molecule or alternatively, to the process of translation of mRNA to produce a peptide, polypeptide, protein or enzyme molecule.

By "operably under control" is meant that a stated first integer is regulated or controlled by a stated second integer.

In the present context, where the expression of the reporter molecule is operably under control of a biological activity, said expression is modified (ie. enhanced, induced, activated, decreased or repressed) when a peptide, oligopeptide or polypeptide capable of enhancing, inducing, activating, decreasing or repressing the formation of said biological activity is expressed. Accordingly, it is not usually sufficient for only one partner in the biological activity to be present or such modified expression of the reporter molecule to occur however, there may be some expression of the reporter molecule in the presence of only one partner.

As used herein, the term "peptide library" is a set of diverse nucleotide sequences encoding a set of amino acid sequences, wherein said nucleotide sequences are preferably contained within a suitable plasmid, cosmid, bacteriophage or virus vector molecule which is suitable for maintenance and/or replication in a cellular host. The term "peptide library" further encompasses random amino acid sequences derived from a known genomic sequence, wherein the amino acid sequences are encoded by a second nucleotide sequence obtained for example by shearing or partial digestion of genomic DNA using restriction endonucleases or nucleases such as Dnase1, amongst other approaches.

Preferred peptide libraries according to this embodiment of the invention are "representative libraries", comprising a set of amino acid sequences or nucleotide sequences encoding same, which includes virtually all possible combinations of amino acid or nucleotide sequences for a previously defined and specified length of peptide or nucleic acid molecule, respectively.

In a particularly preferred embodiment of the invention, the peptide library comprises cells, virus particles or bacteriophage particles comprising a diverse set of nucleotide sequences which encode a diverse set of amino acid sequences, wherein the member of said diverse set of nucleotide sequences are placed operably under the control of a promoter sequence which is capable of directing the expression of said nucleotide sequence in said cell, virus particle or bacteriophage particle.

Accordingly, the amino acid sequence encoded by the second nucleotide sequence may comprise any sequence of amino acids of at least about 1 to 100 amino acids in length and preferably 1 to 60 amino acids in length and may be derived from the expression of known nucleotide sequences which are prepared by any one of a variety of methods such as, for example, random synthetic generation. More preferably, the peptide unit is a 6 to 20 amino acid peptide. The use of larger nucleotide fragments, particularly employing randomly sheared nucleic acid derived from bacterial, yeast or animal genomes, is not excluded.

Alternatively or in addition, the amino acid sequence may be expressed as a fusion protein with a nuclear targeting motif capable of facilitating targeting of said peptide to the nucleus of said host cell where transcription occurs, in particular the SV40 nuclear localisation signal which is functional in yeast and mammalian cells.

Alternatively, or in addition, the amino acid sequence may be expressed as a fusion protein with a peptide sequence capable of enhancing, increasing or assisting penetration or uptake of the peptide by an isolated cell such as when the subject amino acid sequence is synthesized ex vivo and added to isolated cells in culture. In a particularly preferred embodiment, the peptide sequence capable of enhancing, increasing or assisting penetration or uptake is functional in higher eukaryotic cells; for example the Drosophila penetratin targeting sequence. According the this embodiment, the fusion protein at least comprises the amino acid sequence:

CysArgGlnIleLysIleTrpPheGlnAsnArgArgMetLysTrpLysLys (Xaa)$_n$ Cys [Seq. ID NO: 1]

or a homologue, derivative or analogue thereof, wherein Xaa is any amino acid residue and n has a value greater than or equal to 1. Preferably, the value of n will be at least 5, more preferably between about 5 and about 20, even more preferably between about 15 and about 35 and still even more preferably between about 30 and about 50 and still more preferably between about 35 and about 55. In a still more preferred embodiment, the value of n is between at least about 40 and at least about 60.

Reference herein to a "promoter" is to be taken in its broadest context and includes the transcriptional regulatory sequences of a classical genomic gene, including the TATA box which is required for accurate transcription initiation in eukaryotic cells, with or without a CCAAT box sequence and additional regulatory elements (i.e. upstream activating sequences, enhancers and silencers). Promoters may also be lacking a TATA box motif, however comprise one or more "initiator elements" or, as in the case of yeast-derived promoter sequences, comprise one or more "upstream activator sequences" or "USA" elements. For expression in prokaryotic cells such as bacteria, the promoter should at least contain the −35 box and −10 box sequences.

A promoter is usually, positioned upstream or 5', of a structural gene, the expression of which it regulates. Furthermore, the regulatory elements comprising a promoter are usually positioned within 2 kb of the start site of transcription of the gene.

In the present context, the term "promoter" is also used to describe a synthetic or fusion molecule, or derivative that confers, activates or enhances expression of the subject reporter molecule in a cell. Preferred promoters may contain additional copies of one or more specific regulatory elements, to further enhance expression of the gene and/or to alter the spatial expression and/or temporal expression. For example, in yeast regulatory elements that confer galactose, phosphate or copper inducibility may be placed adjacent to a heterologous promoter sequence driving expression of the reporter, thereby conferring conditional inducibility on the expression of said gene by the addition of the appropriate inducer to the growth medium.

Placing a gene operably under the control of a promoter sequence means positioning the said gene such that its expression is controlled by the promoter sequence. Promoters are generally positioned 5' (upstream) to the genes that they control. In the construction of heterologous promoter/structural gene combinations it is generally preferred to position the promoter at a distance from the gene transcription start site that is approximately the same as the distance between that promoter and the gene it controls in its natural setting, i.e., the gene from which the promoter is derived. As is known in the art, some variation in this distance can be accommodated without loss of promoter function. Similarly, the preferred positioning of a regulatory sequence element with respect to a heterologous gene to be placed under its control is defined by the positioning of the element in its natural setting, ie. the genes from which it is derived. Again, as is known in the art some variation in this distance can also occur.

Examples of promoters suitable for use in regulating the expression of the reporter molecule and/or amino acid sequence and/or the polypeptide binding partner in a cell include viral, fungal, yeast, insect, animal and plant derived promoters. Preferred promoters are capable of conferring expression in a eukaryotic cell, especially a yeast or mammalian cell. The promoter may regulate the expression of a gene constitutively, or differentially with respect to the tissue in which expression occurs or, with respect to the developmental stage at which expression occurs, or in response to external stimuli such as environmental stress, or hormones amongst others.

Particularly preferred promoters according to the present invention include those naturally occurring and synthetic promoters which contain binding sites for transcription factors, more preferably for helix-loop-helix (HLH) transcription factors, zinc finger proteins, leucine zipper proteins and the like. Preferred promoters may also be synthetic sequences comprising one or more upstream operator sequences such as LexA operator sequences or activating sequences derived from any of the promoters referred to herein such as GAL4 DNA binding sites.

Those skilled in the art will recognise that the choice of promoter will depend upon the nature of the cell being transformed and the molecule to be expressed. Such persons will be readily capable of determining functional combinations of minimum promoter sequences and operators for cell types in which the inventive method is performed.

In a particularly preferred embodiment, the promoter is a yeast promoter, mammalian promoter, a bacterial or bacteriophage promoter sequence selected from the list comprising GAL1, CPU1, PGK1, ADH2, PHO5, PRB1, GUT1, SPO13, ADH1, CMV, SV401 T7, SP6, lac or tac promoter sequences.

Whilst the invention is preferably performed in yeast cells, the inventors clearly contemplate modifications wherein the invention is performed entirely in mammalian cells, utilising promoters that are operable in mammalian cells to drive expression of the various assay components, in combination with a counter selective reporter gene operable in mammalian cells. Such embodiments are within the ken of those skilled in the art.

For expression in mammalian cells, it is preferred that them promoter is the CMV promoter sequence, more preferably the CMV-IE promoter or alternatively, the SV40 promoter and, in particular, the SV40 late promoter sequence. These and other promoter sequences suitable for expression of genes in mammalian cells are well known in the art.

Examples of mammalian cells contemplated herein to be suitable for expression include COS, VERO, HeLa, mouse C127, Chinese hamster ovary (CHO), WI-38, baby hamster kidney (BHK) or MDCK cells lines, amongst others. A wide variety of cell lines such as these are readily available to those skilled in the art.

The prerequisite for producing intact polypeptides in bacterial cells and, in particular, in *Escherichia coli* cells, is the use of a strong promoter with an effective ribosome binding site, such as a Shine-Dalgarno sequence, which may be incorporated into expression vectors carrying the first and second nucleotide sequences, or other genetic constructs used in performing the various alternative embodiment of the invention. Typical promoters suitable for expression in bacterial cells such as *E. coli* include, but are not limited to, the lacZ promoter, temperature-sensitive $\lambda_L$ or $\lambda_K$ promoters, SP6, T3 or T7 promoter or composite promoters such as the IPTG-inducible tac promoter. A number of other vector systems for expressing the nucleic acid molecule of the invention in *E. coli* are well known in the art and are described for example in Ausubel et al (1987) and/or Sambrook et al (1989). Numerous sources of genetic sequences suitable for expression in bacteria are also publicly available in various plasmid constructs, such as for example, pKC30 ($\lambda_L$), pKK173-3 (tac), pET-3 (T7) or the pQE series of expression vectors, amongst others.

Suitable prokaryotic cells for expression include *Staphylococcus, Corynebacterium, Salmonella, Escherichia coli, Bacillus sp.* and *Pseudomonas sp.* amongst others. Bacterial strains that are suitable for the present purpose are well known in the relevant art.

Where the promoter is intended to regulate expression of the reporter molecule, it is particularly preferred that said promoter include one or more recognition sequences for the binding of a DNA binding domain derived from a transcription factor, for example a GAL4 binding site or LexA operator sequence.

As used herein, the term "reporter molecule" shall be taken to refer to any molecule that is capable of producing an identifiable or detectable result.

In one embodiment of the invention, the reporter molecule is an enzyme, peptide, oligopeptide or polypeptide that comprises a visible product or at least, when incubated in the presence of a substrate molecule can convert said substrate to a visible product, such that cells expressing the reporter molecule may be readily detected. For example, the expression of reporter genes that encode polypeptides, which themselves fluoresce, or cause fluorescence of a second molecule, can be operably connected to the biological activity being assayed, to facilitate the detection of cells wherein expression of the reporter molecule is present or absent. Such applications are particularly useful in high throughput drug screening approaches, wherein it is desirable to rapidly screen a large number of drug candidates for their agonist/antagonist properties with respect to the biological activity in question. Preferred reporter molecules according to this embodiment include, but are not limited to, the *Escherichia*

*coli* β-galactosidase enzyme, the firefly luciferase protein and the green fluorescent protein or mutants thereof which possess red-shifted or blue-shifted emission spectra or enhanced output. Persons skilled in the art will be aware of how to utilise genetic sequences encoding such reporter molecules in performing the invention described herein, without undue experimentation. For example, the coding sequence of the gene encoding such a reporter molecule may be modified for use in the cell line of interest (eg. human cells, yeast cells) in accordance with known codon usage preferences. Additionally, the translational efficiency of mRNA derived from non-eukaryotic sources may be improved by mutating the corresponding gene sequence or otherwise introducing to said gene sequence a Kozak consensus translation initiation site.

Preferably, the reporter molecule allows colorometric identification of its expression either by direct fluorescence (eg. Green Fluorescent Protein) or by a change in colour in the presence of an appropriate substrate (eg. the production of a blue colour with β-galactosidase in the presence of the substrate 5-bromo-4-chloro-3-indoyl-β-D-galacotside (ie. X-GAL).

Particularly preferred reporter molecules according to the present invention are those which produce altered cell growth or viability, including the ability to induce cell death. In the present context, the reporter molecule either comprises the first nucleic acid molecule or is encoded by said first nucleic acid molecule. Accordingly, those skilled in the art will be aware that the reporter molecule of such an embodiment is preferably a peptide, polypeptide, enzyme, abzyme or other protein molecule or alternatively, an isolated nucleic acid molecule.

Preferably, the reporter molecule of the invention is capable of directly or indirectly inhibiting, enhancing or otherwise modulating the growth and/or viability of the host cell. Direct modulation of cell growth and/or viability is where expression of the reporter molecule has a direct consequence on cell growth and/or viability. Indirect modulation of cell growth and/or viability is where expression of the reporter molecule has no direct consequence on cell growth and/or viability, however, said expression may modulate cell growth and/or viability when cells are cultured in the presence of a suitable co-factor or substrate molecule, amongst others.

Where the reporter molecule is a peptide, polypeptide, enzyme, abzyme or other protein molecule which comprises a cytostatic compound, anti-mitotic compound, toxin, mitogen or growth regulatory substance such as a hormone or protein which is essential to cell growth or viability, it may have a direct effect on cell growth or viability when expressed therein. Similarly, a reporter molecule which comprises a nucleic acid molecule may have a direct effect on cell growth and/or viability, for example wherein the reporter molecule is a ribozyme, antisense molecule, minizyme, or co-suppression molecule which is targeted to the expression of a gene which is capable of modifying cell growth and/or viability.

Wherein it is desirable for the reporter molecule to have an indirect effect on cell growth and/or viability, this may be achieved, for example by coupling expression of the reporter molecule to the production of a cytostatic compound, anti-mitotic compound, toxin or negative growth regulatory molecule.

In one embodiment, the reporter molecule is an enzyme which, when expressed in the host cell, catalyses the conversion of a substrate molecule which is not capable of altering or affecting cell growth and/or viability, to produce a product which comprises a toxin, cytostatic compound or anti-mitotic compound. According to this embodiment, the expression of the reporter molecule in the presence of said substrate leads to production of a sufficiently high concentration of the toxin, cytostatic compound or anti-mitotic compound to reduce cell growth or result in cell death.

In a further embodiment, the reporter molecule is an enzyme which, when expressed in the host cell, catalyses the conversion of a cytostatic or anti-mitotic substrate molecule to produce a product which is incapable of modifying cell growth and/or viability. According to this embodiment, cells incubated in the presence of the substrate molecule do not grow or divide as rapidly as cells that are not incubated therewith. Wherein cells incubated in the presence of the cytostatic or anti-mitotic substrate molecule express the reporter molecule, cell division and/or cell growth is resumed when the concentration of said substrate in said cell is reduced.

In an alternative embodiment, the reporter molecule directly or indirectly enhances cell growth and/or viability, for example by coupling expression of the reporter molecule to the production of a mitogen or positive growth regulatory molecule.

In a further embodiment, the reporter molecule is an enzyme which, when expressed in the host cell, catalyses the conversion of a first compound which in active in modulating cell growth and/or viability to produce a mitogen or positive growth regulatory molecule product. According to this embodiment, cells incubated in the presence of the substrate molecule grow and divide at a normal rate compared to other cells. Expression of the enzyme reporter molecule in the presence of the substrate molecule leads to enhanced cells growth and/or cell division as the concentration of the mitogen or positive growth regulatory molecule is increased in the cell. As a consequence, cells in which the reporter molecule is enhanced as a result of the biological activity grow and/or divide more rapidly than the surrounding cells in the library, facilitating their detection.

In the context of the present invention, the amino acid sequence identified using the above method is capable of modulating the expression of the reporter molecule. Accordingly, the amino acid sequence may be an agonist or an antagonist of the biological activity under which expression of the reporter molecule is operably placed. Wherein the amino acid sequence is an agonist molecule, reporter molecule expression will be increased or enhanced or activated and, depending upon whether or not the reporter molecule directly or indirectly increases or reduces cell growth and/or viability, cell growth will be increased or reduced, respectively. In such embodiments of the invention however, it is clearly undesirable for the reporter molecule to result in cell death, because it would not be possible to recover the cells expressing the desired peptide. Wherein the amino acid sequence is an antagonist of the biological activity, reporter molecule expression will be decreased or repressed or inactivated and, depending upon whether or not the reporter molecule directly or indirectly increases or reduces cell growth and/or viability, cell growth will be reduced or increased, respectively. Wherein the reporter molecule leads directly or indirectly to cell death, antagonism of the biological activity by the antagonist amino acid sequence facilitates survival of the cell compared to cells which do not express the antagonist but express the reporter molecule.

Examples of suitable yeast positive selectible reporter genes (suitable for isolation of peptide agonists) include but are not limited to HIS3 and LEU2 the protein products of which allow cells expressing these reporter genes to survive on appropriate cell culture medium. Conversely, several yeast counterselectable reporter genes (suitable for isolation of peptide antagonists) exist, including the URA3 gene, wherein URA3 expression is toxic to a cell expressing this gene, in the presence of the drug 5-fluoro-orotic acid (5FOA). Other counter-selectable reporter genes include CYH1 and LYS2, which confer lethality in the presence of the drugs cycloheximide and alpha aminoadipate (αAA), respectively. For counter selection i bacteria corresponding reporter genes encoding toxic products are available, including: SacB, CcdB and the mammalian GATA-1 gene, the expression of which is toxic in E. coli.

Standard methods are used to introduce the first and second nucleotide sequences into the cellular host. In the case of yeast cells, this may be achieved by mass mating or transformation.

In one embodiment, the first and second nucleotide sequences are each contained within a separate genetic construct, further comprising a selectable marker gene to facilitate detection of transformed cells, for example an antibiotic resistance selectable marker gene. Preferably, the selectable marker genes for each genetic construct are different, such that the presence of one or both genetic constructs in a single cell may be facilitated. The first and second nucleotide sequences may thus be introduced into the cellular host by shotgun cotransformation and selection on an appropriate media to select for the presence of both selectable marker genes.

Alternatively, the first and second nucleic acid sequences may be introduced by sequential transformation, accompanied by selection for the appropriate marker genes after each transformation event.

Alternatively, the first and second nucleotide sequences may be introduced into separate populations of host cells which are subsequently mated and those cell populations containing both nucleotide sequences are selected on media permitting growth of host cells successfully transformed with both first and second nucleic acid molecules.

Alternatively, the first and second nucleotide sequences may be contained on a single genetic construct and introduced into the host cell population in a single step. In such an embodiment of the invention, the random peptide library is usually produced using a vector which at least comprises the first nucleotide sequence placed operably under control of a suitable promoter with or without operator sequence, and a selectable marker gene, the insertion site for the second nucleotide sequence being selected such that the inserted second nucleotide sequence is capable of being expressed.

These embodiments are in addition to the steps to be performed in relation to the introduction of one or more further nucleic acid molecules that encode one or more polypeptide binding partners of the biological activity, variations of which are described supra.

The genetic construct may be in the form of an autonomously replicating vector or may comprise genetic sequences to facilitate integration into a host cell genome.

Alternatively, the first nucleotide sequence encoding the reporter molecule can be integrated into the chromosome of the host cell by homologous recombination of the products of polymerase chain reaction (PCR), or of sequences on another DNA molecule that is incapable of replicating autonomously in yeast cells.

According to the nature of the biological activity of interest, the first nucleotide sequence may be placed operably in connection with any promoter sequence, the only requirement being that the promoter is capable of regulating gene expression in the host cell selected. Usually, the host cell will be varied to suit the promoter sequence. The present invention clearly extends to the isolation of peptides capable of modulating any biological activity.

In fact, the present invention will facilitate the identification and isolation of a amino acid sequences that modulates or mediate expression of a reporter molecule by agonising or antagonising any regulatory step which is required for expression to occur, not merely steps later in the signal transduction pathway, such as DNA-protein interactions or interactions between transcription factors. Wherein it is desired to isolate a specific amino acid sequence which is capable of modulating a particular biological activity, it is necessary only to operably connect expression of the first nucleotide sequence to the biological activity of interest. This is done by placing the first nucleotide sequence operably in connection with a promoter sequence which is regulated by the biological activity or alternatively, genetically manipulating a promoter sequence which is operably connected to the first nucleic acid molecule thereby placing the promoter under operable control of the biological activity.

In the case of amino acid sequences that modulate or mediate a protein:DNA interaction which is required for gene expression or the modulation of gene expression, for example to isolate a peptide molecule which interacts directly with a cis-acting enhancer or silencer element or a protein to which said element binds, this objective may be achieved by introducing the cis-acting element into a promoter sequence to which the first nucleotide sequence is operably connected. By this means, expression of the reporter molecule is placed operably under the control of the cis-acting element and modulation of gene expression will occur when the appropriate protein molecule either binds to the cis- acting DNA element or to the protein that recognises said element.

In the case of a protein:protein interaction controlling gene expression, the promoter controlling the expression of the first nucleic acid molecule is selected such that it contains the necessary cis-acting elements to which at least one of the proteins involved in the interaction binds. Where there is not complete knowledge of the cis-acting sequences or trans-acting factors involved in regulating gene expression, but the promoter sequence and cell-type in which expression occurs are known, the first nucleotide sequence may be placed operably in connection with that promoter sequence and the resulting nucleic acid molecule introduced into the cell type. Such a relationship forms the basis of "two-hybrid" screening approaches. Wherein the peptide of interest antagonists or agonises any step required for expression or the activation, repression or enhancement of gene expression, the effect will be identified by recording altered expression of the reporter molecule.

The present invention further contemplates the detection of amino acid sequences that modulate a biological activity, in a mammalian cell, wherein expression of the counter-selectable reporter gene is placed operably under the control of a mammalian-expressible promoter sequence, which is aberrantly active in the pathogenic situation, for example an oncogene promoter such as MYC. Activity of such a promoter would be blocked directly in cells express an amino acid sequence capable of inhibiting the oncogene promoter in a mammalian cell.

In a preferred aspect of the sixth embodiment there is provided a method for identifying a amino acid sequence which is capable of antagonising a protein:protein interaction in a host cell said method comprising the steps of:

(i) producing a peptide library in a cellular host wherein the transformed cells of said library contain at least a first nucleotide sequence which comprises or encodes a reporter molecule capable of reducing the growth and/or viability of said host cell, the expression of which is operably under control of said protein:protein interaction and a second nucleotide sequence derived from a defined genomic sequence which is capable of encoding said amino acid sequence when placed operably under the control of a suitable promoter sequence and wherein (b) substantially all of the defined genomic sequence is present within the population of transformed cells making up said library.

(ii) culturing said cellular host for a time and under conditions sufficient for expression of said second nucleotide sequence to occur; and (iii) selecting cells wherein expression of said reporter molecule is antagonised, repressed or reduced.

Preferably, the subject method includes the additional first step or later step of introducing into the cellular host one or more further nucleic acid molecules which encode one or more polypeptide binding partners which are involved in the biological activity, operably under the control of one or more promoter sequences. Such embodiments are described in detail supra.

According to this embodiments, it is preferred that the reporter molecule comprise a peptide, polypeptide, enzyme, or other protein molecule which is capable of converting an innocuous substrate molecule into a cytostatic compound, anti-mitotic compound or a toxin, such that antagonised expression of the reporter molecule by the subject peptide prevents cell death or at least prevents a reduction in cell growth and/or viability in the presence of the substrate. More preferably, in the yeast system, the reporter gene is URA3 and/or CYH2, amongst others such as LYS2. In a particularly preferred embodiment, the reporter molecule is the product of the URA3 gene which, when expressed converts 5-fluoroorotic acid (5-FOA) to a toxic product.

One exemplification of this embodiment takes advantage of the fact that most active eukaryotic transcription activators are modulator and comprise a DNA binding domain and a DNA activation domain, wherein the DNA binding domain and the DNA activation domain may be contained on the same protein molecule or alternatively, on separate molecules which interact to regulate gene expression. According to this embodiment, the expression of the reporter molecule is placed operably under the control of a protein:protein interaction, for example between the oncogenic proteins SCL and LMO2 which bind to form an active artificial transcription factor. The transcription of the reporter gene can therefore be used as an indicator of two proteins interacting where one of said proteins of interest comprises at least a DNA binding domain and binds to an operator promoter element upstream of the reporter gene and said other protein of interest comprises at least a DNA activation domain. Binding of the DNA binding protein to the operator, in the presence of a function activation domain, initiates transcription of the reporter gene. The URA3 reporter thereby acts as a counter selectable marker.

This embodiment of the invention may be adapted to the identification of amino acid sequences which modulate other protein:protein interactions, by functionally replacing the DNA binding domain of transcription factor with a different DNA binding domain which is specific for a different cis-acting element in the promoter regulating expression of the reporter molecule. Methods for the production of such fusion proteins are well known to those skilled in the art. In such cases, the selection of an appropriate DNA binding domain will depend on the nature of the DNA binding site located upstream of the reporter gene.

For example, fusion proteins may be constructed between an oncoprotein and a DNA binding domain and/or a DNA activation domain. For example, a sequence of nucleotides encoding or complementary to a sequence of nucleotides encoding residues 176 to 331 of SCL may be fused to the LexA DNA binding domain and a nucleotide sequence encoding LMO2 may be fused to a DNA activation domain (or vice-versa).

The present invention is also particularly useful for identifying amino acid sequences that inhibit protein protein:protein interactions which normally produce deleterious effects (apart from the deleterious effect of certain reporter molecules), for example interactions involving oncogene products. Specific examples of oncogenes, the products of which form transcription factors contributing to tumorigenesis, include SCL and any one or more of DRG, E47 and/or LMO2.

In a further aspect of the sixth embodiment there is provided a method for identifying a amino acid sequence that is capable of modifying a protein:protein interaction in a host cell, said method comprising the steps of:

(i) producing a peptide library in a host wherein (a) the transformed cells of said library contain: (1) at least a first nucleotide sequence which comprises or encodes a reporter molecule wherein said nucleotide sequence is operably connected to an operator sequence or transcription factor binding site; (2) a second nucleotide sequence derived from a defined genomic sequence which encodes said amino acid sequence when placed operably under the control of a suitable promoter sequence; and (3) one or more further third nucleotide sequences which encode one or more polypeptides, protein or fusion proteins wherein at least one of said polypeptides, proteins or fusion proteins includes at least one DNA binding domain capable of binding to said operator sequence or transcription factor binding site and at least one of said polypeptides, proteins or fusion proteins includes at least one DNA activation domain or derivative thereof capable of activating the expression of said first nucleotide sequence when targeted to the promoter/operator by interaction with another protein bearing the cognate DNA binding domain; and (b) substantially all of the defined genomic sequence is present within the population of transformed cells making up said library;

(ii) culturing said host cell for a time and under conditions sufficient to permit expression of said second and further nucleotide sequences to occur; and (iii) selecting cells wherein expression of said reporter molecule is activated, inhibited or otherwise modified.

The proteins involved in the biological activity of interest, which are encoded by the second nucleic acid molecule, are synthesised in the host cell, either encoded by one or more foreign nucleotide sequences transformed into the host cell or integrated into the genome of said cell. However, the present invention clearly extends to situations in which these sequences are also encoded by endogenous host cell genes.

According to this embodiment, the DNA binding domain binds to the operator sequence and, in the presence of the DNA activating region, expression of the reporter molecule occurs. Wherein the second nucleotide sequence encoders a peptide that antagonises or inhibits DNA binding and/or DNA activation, expression of the reporter molecule is repressed, reduced or otherwise inhibited. Alternatively, wherein the second nucleotide sequence encodes an amino acid sequence that agonises or enhances DNA binding and/or DNA activation, expression of the reporter molecule is activated, enhanced or otherwise increased.

Those skilled in the art will recognise that the DNA binding domain and the DNA activation domain may be contained on a single amino acid molecule or alternatively, they may be contained in separate amino acid molecules that interact with each other to regulate reporter gene expression.

Similarly, the first and/or second and/or further nucleotide sequences may be contained on a single nucleic acid molecule, for example in one genetic construct or alternatively, one, two, three or more of said sequences may be contained on separate nucleic acid molecules. Wherein one or more of the nucleotide sequences are contained on separate nucleic acid molecules, then each such nucleotide sequence is further preferably operably connected to its own promoter sequence. Alternatively, where any two or more of the nucleotide sequences are contained on the same nucleic acid molecules, the nucleotide sequences may be expressed under the control of a single promoter or alternatively, under the control of separate promoter sequences.

Those skilled in the art will recognise that the alternatives described supra are equally applicable to this embodiment of the invention.

In a further preferred aspect of the sixth embodiment, the subject method further comprises the step of isolating the second nucleotide sequence from the host cell and sequencing the nucleic acid molecule and deriving the amino acid sequence encoded thereof. Once the sequence has been identified it can then be compared to like sequences in within the known nucleotide sequence to identify those amino acids which are essential for modulation of biological activity. Synthetic peptides may then be produced, based upon the derived amino acid sequence thus obtained. Those skilled in the art are well versed in such techniques.

The present invention also contemplates amino acid sequences identified by the method of the present invention.

Preferably the amino acid sequences are agonists or antagonists of protein:protein or protien:DNA interactions. More preferably, the peptides, oligopeptides and polypeptides of the present invention are antagonists of protein:protein interactions or protein:DNA interactions and even more preferably, antagonists of protein:protein interactions.

In a particularly preferred embodiment, the peptides of the invention antagonise or inhibit interactions that produce deleterious effects in eukaryotic cells, in particular human or animal cells. More preferably, the amino acid sequences of the invention antagonise or inhibit interactions which involve one or more oncoproteins.

The present invention clearly contemplates the use of said amino acid sequences or fragments or derivatives hereof in the prophylactic or therapeutic treatment of human or animal. Methods of treatment include their use in antibiotic peptide therapy regimens such as in the treatment protocols for patients with bacterial, fungal or viral infections. Their use in treatment protocols for said patients includes their administration as a means of inhibiting the growth of the infecting microorganism and/or inhibiting its virulence. The use of such peptides in potentiating the effects of other antimicrobial agents is also envisaged (eg. See international PCT application: WO 96/24684).

Accordingly, another aspect of the present invention contemplates a pharmaceutical composition comprising a peptide, oligopeptide and polypeptide that is capable of modulating a biological activity and one or more pharmaceutically acceptable carriers and/or diluents.

A preferred embodiment contemplates a pharmaceutical composition wherein said peptide, oligopeptide and polypeptide antagonises the growth and/or virulence of a pathogen, and one or more pharmaceutically acceptable carriers and/or diluents. These components are referred to as the active ingredients.

The pharmaceutical forms suitable for injectable use include sterile aqueous solutions (where water-soluble) or dispersions and sterile powders for the extemporaneous preparation of sterile injectable solutions or dispersion or may be in the form of a cream or other form suitable for optical application. Alternatively, injectable solutions may be delivered encapsulated in liposomes to assist their transport across cell membrane. Alternatively or in addition such preparation may contain constituents of self-assembling bore structures to facilitate transport across the cellular membrane. It must be stable under the conditions of manufacture and storage and must be preserved against the contaminating/destructive action of environmental microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as licithin, by the maintenance of the required particle size in the case of dispersion and by the use of superfactants. Prevention of the action of microorganisms can be brought about by various antibacterial and antifungal agents, for example, parabens, chlorobutanol, phenol, sorbic acid, thirmerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active ingredients are suitably protected they may be orally administered, for example, with an inert diluent or with an assimilable edible carrier, or it may be enclosed in hard or soft shell gelatin capsule, or it may be compressed into tablets, or it may be incorporated directly with the food of diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained. Preferred compositions or preparations according to the present invention are prepared so that a dosage unit form contains between about 0.1 $\mu$g and 20 g of active compound.

The tables, troches, pills, capsules and the like may also contain the components as listed hereafter: A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

The present invention also extends to forms suitable for topical application such as creams, lotions and gels.

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form of ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form. A unit dosage form can, for example, contain the principal active compound in amounts ranging from 0.5 µg to about 2000 mg. Expressed in proportions, the active compound is generally present in from about 0.5 µg to about 2000 mg/ml of carrier. In the case of compositions containing supplementary active ingredients, the dosages are determined by reference to the usual dose and manner of administration of the said ingredients.

The pharmaceutical composition may also comprise genetic molecules such as a vector capable of transfecting target cells where the vector carries a nucleic acid molecule capable of inhibiting such deleterious biological interaction/ activities. The vector may, for example, be a viral vector.

EXAMPLES

Further features of the present invention are more fully described in the following non-limiting Examples. It is to be understood, however, that this detailed description is included solely for the purposes of exemplifying the present invention. It should not be understood in any way as a restriction on the broad description of the invention as set out above.

Methods of molecular cloning, immunology and protein chemistry that are not explicitly described in the following examples are reported in the literature and are known by those skilled in the art. General texts that described conventional molecular biology, microbiology, and recombinant DNA techniques within the skill of the art, included, for example: Sambrook et al. *Molecular Cloning; Laboratory Manual,* Second Edition, Cold Spring Harbor Laboratory Press, Cold Spring Harbor, N.Y. (1989); Glover ed., *DNA Cloning: A Practical Approach,* Volumes I and II, MRL Press, Ltd. Oxford, U.K. (1985); and Ausubel, F., Brent, R., Kingston, R. E., Moore, D. D., Seidman, J. G., Smith, J. A., Struhl, K. *Current protocols in molecular biology.* Greene Publishing Associates/Wiley Intersciences, New York.

Example 1

The Construction of Biodiverse Gene Fragment Libraries

The genomic DNA of a diverse panel of microorganisms, chosen to maximise the genetic diversity across the panel, were reduced to fragments suitable for expressing peptides. Techniques suitable for achieving this outcome include: mechanical shearing, partial DNA-asel digestion and the use of combinations of restriction endonuclease.

Each genome was then added to the pool in direct proportion to its size and complexity. More DNA of large genomes was added than small genomes to ensure adequate representation.

A peptide library was then constructed by digesting aliquots of the polled DNA with all 6 combinations of 2 restriction enzymes for a set containing Alu I, Bst U I, Hae III and Rsa I. These enzymes are blunt-cutting restriction endonculeases, which have distinct 4 base pair recognition sequences and thus each combination will produce fragments with sizes in the 90–120 bp range predominating. These are suitable for cloning and the length of DNA is sufficient to encode peptides of about 30 amino acid residues that are in the range of the sizes of sequences reported in structurally conserved regions of proteins. In instances where linkers rather than adaptors are to be ligated to the genomic fragments, the genomic digest pool may be protected from subsequent digestion by treatment with an appropriate methylase (in this example EcoR1 methylase).

The digest fragments were purified by native acrylamide gel electrophoresis followed by gel filtration chromatography.

Linkers were then ligated onto the DNA fragments by standard methods. 3 reading frames of linkers were used. Where the fragments are to be cloned into an EcoR1 site, equimolar amounts of the following 3 self-annealing linkers may be used:

d(pGGAATTCC), d(pCGGAATTCCG)    SEQ. ID NO:3 and d(pCCGGAATTCCGG)    [SEQ. ID NO:4]

Where the cloning was intended to be directional, an equimolar amount of another linker corresponding to the second 3' restriction site was added—e.g., for cloning into EcoR1 and HindIII sites of a vector (eg., an equal number of moles (to the combined EcoR1 linkers) of the following linker was added to the ligation:

d(pCCAAGCTTGG)    SEQ. ID NO: 5

Linkers were then digested with the restriction endonuclease/s corresponding to their recognition sequences and appropriately sized digest fragments were purified by standard techniques including: agarose gel electrophoresis, sucrose or potassium acetate gradients, or size exclusion chromatography.

the genomic fragments which contain flanking linkers or adaptors (see example 4 below) were then cloned into a pT7-Select expression vector by standard methodology for library construction.

Example 2

BGF Library Construction

Biodiverse gene fragment libraries can be constructed using adapted fragments of pooled genomic DNA from an evolutionarity diverse set of compact genomes. To maximise the diversity of the pool, the relative concentration of DNA in the pool from larger genomes can be increased in proportion to the total haploid genome size. The genomic inserts can be fragmented using mechanical shearing (e.g. sonication) followed by repair and ligation of linker oligonucleotides or adaptors. Alternatively, they can be made by polymerase extension of partially degenerate oligonucleotides anealed to the denatured genomic DNA, followed by amplification using the polymerase chain reaction (PCR).

In this example the oligonucleotides used in the primary extension with the Klenow fragment of DNA polymerase-I (at 15–25 degrees celcius), had the sequence: (Using * to represent a universal base such as 5-nitro-indole)

```
Forward primer: GACTACAAGGACGACGACGACAAGNNNNNNNN*    [Seq. ID NO: 6]
Reverse primer: ATTCCCGGGAAGCTTATCAATCAATCANNNNNNNN*  [Seq. ID NO: 7]
```

N corresponded to degenerate nucleotides (e.g., either dATP, dCTP, dGTP or dTTP). Moreover, either of the universal bases: deoxyinosine, or 5-Nitroindole (or functionally equivalent analogue) can be substituted at any or all of the 'N' positions of the primer, especially at the 3' terminal position. Thus the length of the 'N' series can varied from 6 to 8 nucleotides.

According to this example, the primers for the nested PCR amplification of the product of the Klenow extension reaction were:

```
Forward primer: GAGAGGAATTCAGACTACAAGGACGACGACGACAAG  [Seq. ID NO: 8]
Reverse primer: GAGAGAATTCCCGGGAAGCTTATCAATCAATCA.    [Seq. ID NO: 9]
```

The PCR amplification were performed using a 'Touchdown' protocol with 'hot-start' enzyme to maximise specificity.

The initial extension and PCR amplification was performed entirely with Klenow polymerase adding more polymerase each cycle as in the initial report of PCR. This allows the entire cycling to be performed between the denaturation temperature (90–100 degrees celcius) and a low, annealing temperature (15–25 degrees celcius), minimising the potential annealing bias against amplification of A/T rich sequences. For this approach the primers had the form:

```
Forward primer: GAGAATTCANNNNNNNN*   [Seq. ID NO: 10]
Reverse primer: GAGAATTCNNNNNNNN*    [Seq. ID NO: 11]
```

Methylated nucleotides can be included in the PCR reaction (but not incorporated into the primers) to protect the products from internal cleavage with restriction enzymes during cloning.

In a preferred form of the example, mutagenic PCR using alternative nucleotides and/or the use of a manganese buffer can also be employed to increase the sequence diversity of inserts.

The resultant PCR products were digested with EcoR1 alone or EcoR1 and Xmal (where the reverse primer contains an Xmal site prior to cloning into vectors of the pBLOCK series.

Libraries were constructed according to standard methodology using the highest efficiency commercially available competent cells viz. XL10-Gold (Stratagene) to ensure complexities greater than $10^7$ independent clones.

Example 3

Mimotope Libraries Using Biodiverse Gene Fragments

This example illustrates the detection of mimotopes from the major house dust mite allergen Der p 1.

DNA in the 90–120 bp range of each of the double digests was isolated and poled, ligated to linkers in all reading frames and cloned into phage display vector T7 Select 1.1 or the vector T7 Select 415. Some DNA fragments were outside the range of 90–120 bp range and were not cloned, but the redundancy in the digestion procedures should allow a representation of most sequences. The use of a pool of 3 reading frames of linkers and/or a translational slippage signal in the construction of the library ensured that all 6 reading frames of the inserts were represented. The total genome size of a biodiverse panel of microorganisms was approximately 35 Mb. This procedure generated about $12 \times 10^6$ different fragments allowing for cloning in all reading frames and orientations. Allowing for the latter about $\frac{1}{6}^{th}$ of the sequences encoded natural peptides. The T7Select is a molecular cloning system with high packing efficiency and is designed to display the peptides encoded by the cloned DNA as C-terminal fusions on a phage coat protein which is accessible for affinity purification procedures. A minority of the unnatural peptides were smaller than the estimated size range because they will be truncated by stop codons. The T7 Select 1.1 or the vector T7 Select 415 display the peptide in low and high copy number so high and low affinity interactions can be used for affinity purification.

Further diversity was generated by PCR mutagenesis which conducts the amplification under conditions which favour high error rates. It has been calculated with an error rate of 0.5 bases per 100 bp/cycle (which can be achieved) that eight mutagenic cycles produces base changes in 90% of the PCR products and almost 50% will have 2 to 3 substitutions. Linkers were added to provide the primer sequences for the PCR and a final high fidelity PCR was performed with linkers extended to provide cloning sites. The mutated fragments had a 10x diversification of the sequences in an amount of DNA which was readily packaged.

Phage from the libraries constructed above which display peptides which bind to human and murine IgG and IgE anti-Der p 1 were isolated using methods based on those described for pollen allergens [11] and other antigens. They are essentially standard protocols for affinity purifying phage displaying antigens. Such methods have been described for filamentous phage display systems and the T7Select cloning system.

Antibody was affinity purified from Der p 1-coupled Sepharose™ and used to coat ELISA wells to immunoselect phage by a panning procedure. Several cycles of selection and phage amplification were performed as recommended. Several types of affinity purification methods have been used for selecting phage so there is scope to use a variety of procedures. Human IgE antibodies were isolated from the serum of allergic subjects and IgG from the serum of allergic and nonallergic subjects. Monoclonal mouse IgG antibodies which are known to recognizes a different epitope were used to isolate peptides which minimic different epitopes.

Following selection and amplification of the phase displaying the peptides further purification may be obtained using plaque immunoassays performed with anti Der p 1 antibodies [11; 12]. Such a procedure enables the isolation of individual clones reacting with the antibodies. Crossover immunoassays were performed with different human and mouse antibody preparations to estimate the frequency of, and to isolate shared peptide mimotopes. Phage were then selected for further study based on the sequence of the peptide, the serological reactivity and intended use. The specificity of the antibody mimotope interaction was tested by inhibition assays against other purified mite allergens and by Western blotting of antiserum against complex protein sources, allergen and microbial extracts.

The antibody binding activity of mimotopes can often be improved by fine adjustments of the amino acid sequence. Clones encoding peptides reacting with anti Der p 1 were optimized for antibody binding by random mutagenesis using PCR enhanced for mismatching by Mn++ and high nucleotide concentrations. The sequences flanking cloning site will be used for the primers. A final high fidelity PCR using the primers extended to contain the restriction enzyme sequences for recloning into display vector was performed for cloning. The phage containing the mutated inserts were then used to transform E. coli and produce plaques for immunoscreening. Clones showing the highest antibody binding activity were picked.

The peptides identified by the described purification procedure were tested for their ability to not minimic the an epitope of the Der p 1 allergen but to be a mimotope which can immunise animals or humans to induce anti Der p 1 antibodies. This was performed in the following ways: with a synthetic peptide chemically coupled to an immunogenic carrier, with peptide genetically fused to a carrier by molecular cloning techniques and by using the phage displaying the peptide as immunogens.

The ability of the peptides to bind to IgE against the Der p 1 allergen can be used for diagnostic techniques which not only detect the presence of antibody but which can also show the diversity of the immune response and pattern of epitope recognition. The ability to act as a mimotope and induce anti-allergen IgG antibody can be used in several immunotherapeutic strategies. Importantly constructs can be produced to enable the peptide to be used as a monovalent immunogen and thus prevent allergens reaction cause by cross-linking IgE molecules in allergic patients.

Example 4

Screening Peptide Libraries Encoding Biodiverse Gene Fragments for Antimicrobial Agents To isolate novel peptides with antibiotic activity against a multi-resistant *Staphylococcus aureus* strain, the following approach was used.

A biodiverse gene fragment library was first made by the procedures described in example 1 in a T7-phage vector. Examples of T7-phage vectors that can be used in this part of the method include: T7Select415-1b. T7Select1-1b. T7Select1-2a. T7Select1-2b and/or, T7Select1-2c (Novagen), having a complexity greater 1,000,000 individual clones.

The library was plated out at a multiplicity of at least one on a lawn of either *E. coli* BL21 (in the case of T7Select415-1b) or either of the complementing hosts *E.coli* BLT5403 of *E.coli* BLT5615 (for the other vectors), to allow a plaque density of below semi-confluence.

The plates used were double-sided, being made in a fashion resembling dual culture plates joined together by the underside. Such plates therefore had two lids on opposite faces. The adjoining face of the two sides of the plates was made of nitrocellulose or nylon membrane, supported by a grid made of a rigid material such as plastic. The opposite side of the plate to the side containing the BL321-derived T7 plaque overlay contained media suitable for the growth of *Staphylococcus aureus*. Following the plating of the library, the *Staphylococcus aureus* was on the face of the plate containing the appropriate media at the minimim density required to obtain a lawn.

The plates were then incubated at 37 degrees Celsius until the T7 phage plaques appear and the *Staphylococcus aureus* lawn appears. Any discontinuities in the lawn of *Staphylococcus aureus* can reflect the diffusion of an inhibitory drug produced by a phage plaque at a corresponding position on the opposite side of the plate. The plaques were then purified to clonality and tested for inhibitory properties in subsequent secondary, tertiary and/or quarternary screens.

The inserts from pure plaques were then amplified using PCR and sequenced using vector primers. The inserts of the clones were then subcloned and purified by standard bacterial expression methodology using vectors such as PET14b, pMAL-c2 or pTYB1, and tested for minimal inhibitory concentration (MIC) by methods known to those skilled in the art.

The sequence of inhibitory peptides can then be used to design synthetic peptide-based candidate drugs which would be tested for animicrobial activity against *Staphylococcus aureus*.

Example 5

Selecting Blockers of Protein/Protein Interactions from Biodiverse Gene Fragment Libraries in Yeast Reverse two hybrid libraries were constructed and screened using the vector pBLOCk-1 as described in our earlier specification (see U.S. Pat. No. 6,610,495, the contents of which are incorporated herein by reference in their entirety) using genomic inserts prepared as described supra in example 1, with the addition of EcoR1 linkers and cloned in to the EcoR1 site of the vector.

Obvious variations of this method will be known to those skilled in the art such as the possibility of using adaptors instead of linkers, of using alternative cloning sites and of including addition sequences into the linkers. For example a pool of the following annealed adaptors could be used in place of the linkers: (Each strand of the adaptor sequence is shown reading 5' to 3').

Adaptor 1
AATTCAATCAATCACACACAGGAGGCCACCATGGATGCATGTGTGCAC    [Seq. ID NO: 12]
GTGCACACATGCATCCATGGTGGCCTCCTGTGTGTGATTGATTG Adaptor 2
AATTCAATCAATCACACACAGGAGGCCACCATGGATGCATGTGTGCA    [Seq. ID NO: 13]
TGCACACATGCATCCATGGTGGCCTCCTGTGTGTGATTGATTG Adaptor 3
AATTCAATCAATCACACACAGGAGGCCACCATGGATGCATGTGTGC    [Seq. ID NO: 14]
GCACACATGCATCCATGGTGGCCTCCTGTGTGTGATTGATTG Adaptors such as those shown here can encode motifs useful for expression or conformational constraint (eg. in this case; dual Shine-Dalgarno and Kozak sequences, flanking cysteine residues and stop codons).

The library was transformed or mated into a yeast strain containing the two proteins whose interaction which one intends to block and containing counter selectable reporter genes whose expression is dependent on that interaction. Detailed methodology for reverse two hybrid screening is described in U.S. Pat. No. 6,610,495.

REFERENCES

1. Tiozzo, E., Rocco, G., Tossi, A. & Romero, D. (1998). *Biochemical and Biophysical Research Communications*, 249, 202–206.
2. Balaban, N., Goldkorn, T., Nhan, R., Dang, L., Scott, R M, R., Rasooly, A., Wright, S., Larrick, J., Rasooly, R. & Carlson, J. (1998). *Science*, 280, 438–440.
3. Colas, P., Cohen, B., Jessen, T., Grishina, I., McCoy, J., Brent, R. (1996). *Nature*, 380, 548–550
4. Xu, C., Mendelsohn, A. & Brent, R. (1997). *Proc.Natl.Acad. Sci. USA*, 94, 12473–12478.
5. Kolonin, M. & Finley, R. (1998). *Roc. Natl. Acad. Sci. USA*, 95, 14266–14271.
6. Derossi, D., Joliot, A. H., Chassaing, G., Prochiantz, A. (1994), *Journal of Biological Chemistry*, 269, 10444–10450.
7. Phelan, A. (1998). *Nature Biotechnology*, 16, 440–443.
8. Marcello, A., Loregion, A., Cross, A., Marsden, H., Hirst, T., Palu, G. (1994). *Proc Natl Acad Sci U.S.A.*, 91, 8994–8998.
9. Fåhraeus, E., Parmaio, J. M., Ball, K. L., Lain, S., Lane, D. P. (1996). *Current Biology*, 6, 84–91.
10. Mennuni, C., Santini, C., Lazzaro, D., Dotta, F., Farilla, L., Fierabracci, A., Bottazzo, G. F., Di Mario, U., Cortese, R. & Luzzago, A. (1997). *Journal of Molecular Biology*, 268, 599–606.
11. Leitner, A., Vogel, M., Radauer, C., Breiteneder, H., Stadler, B. M., Scheiner, O., Kraft, D. & Jensen-Jarolim, E. (1998). *European Journal of Immunology*, 28, 2921–7.
12. Pincus, S. H., Smith, M. J., Jennings, H. J., Burritt, J. B. & Glee, P. M. (1998). *Journal of Immunology*, 160, 293–8.

---

What is claimed is:

1. A method of identifying nucleic acid that encodes a polypeptide that binds to a target protein of mammals wherein said polypeptide does not bind to the target protein in its native environment, said method comprising:
   (a) constructing an expression library using a process comprising:
      (i) producing nucleic acid fragments consisting of 90 base pairs to 120 base pairs in length from genomic DNAs known sequence from a plurality of genomes of different microorganisms or eukaryotes selected from the group consisting of *Fugu rubripes, Caenorhabditis elegans, Saccharomyces cerevisiae, E. coli, Aquifex aeliteus, Methanococcus jannaschii, Bacillus subtilis, Haemophilus influenzae, Helicobacter pylori, Neisseria meningiditis, Syncchocystis sp. Bordetella pertussis, Pasteurella multocida, Pseudomonas aeruginosa, Borrelia burgdorferi, Methanobacterium thermautotrophicum, Mycoplasma pneumoniae, Archaeoglobus fulgidis* and *Vibrio Harvey;*
      (ii) combining the nucleic acid fragments from each genomic in an amount that is proportional to the complexity and size of the genome of said microorganism or eukaryote, thereby enhancing nucleotide sequence diversity among the combined nucleic acid fragments compared to the diversity of sequences in each genome;
      (iii) inserting the combined fragments at (ii) into an expression vector in operable connection with a promoter sequence that confers expression on said fragment in a yeast or bacterial cell, thereby producing a recombinant vector; and
      (iv) introducing the recombinant vector at (iii) into a bacteriophage or a yeast cell or bacterial cell such that a nucleic acid fragment contained therein is expressed to produce a polypeptide;
   (b) screening said expression library by a process comprising determining the binding of the encoded polypeptide to the target protein of mammals to thereby identify a nucleic acid fragment that encodes a polypeptide that binds to the target protein; and
   (c) selecting a nucleic acid fragment at (b) that encodes a polypeptide that binds to the target protein but not in its native environment.

2. The method according to claim 1 further comprising subjecting the fragments to mutagenesis and optionally combining the mutated sequences with non-mutated sequences.

3. The method of claim 2 wherein subjecting the fragments to mutagenesis comprises a process selected from the group consisting of:
   (a) amplifying the fragments using PCR in the presence of manganese; and
   (b) expressing the fragments in cells that are modified to mutate nucleotide sequences.

4. The method of claim 3 wherein the cells do not carry out DNA repair or DNA mismatch repair.

5. The method according to claim 1 wherein inserting the fragments into an expression vector comprises a process selected from the group consisting of:
   (a) ligating the fragments to a linker or adaptor in each of the three possible reading frames for each fragment;
   (b) inserting the fragments into the vector in the forward and reverse orientation;

(c) placing the fragments under the control of nucleic acid that comprises a sequence encoding an internal ribosome entry site (IRES); and (d) placing the fragments under the control of nucleic acid that comprises a sequence that confers transcriptional or translational slippage on said fragment during expression.

6. The method according to claim 1 wherein the nucleic acid fragments have the capacity to encode a peptide consisting of about 30 amino acids in length.

7. The method according to claim 1 further comprising expressing wherein the polypeptide in a conformationally constrained form in a thioredoxin (Trx) loop or with flanking oxidizable cysteine residues.

8. The method according to claim 1 wherein step (iv) comprises introducing the recombinant vector an (iii) into a bacterial cell.

9. The method according to claim 1 wherein step (iv) comprises introducing the recombinant vector at (iii) into a cellular host that is modified to mutate nucleotide sequences.

10. The method of claim 1 wherein step (iv) comprises introducing the recombinant vector at (iii) into a the cellular host that mutates nucleotide sequences by virtue of not carrying out DNA repair or DNA mismatch repair.

11. The method according to claim 1 wherein step (b) comprises assaying expression of the reporter gene said expression being modulated by the binding of the encoded polypeptide to the target protein.

12. The method according to claim 1 wherein the target protein comprises an immunoglobulin.

13. A method of constructing an expression library comprising:

(a) producing nucleic acid fragments consisting of 90 base pairs to 120 base pairs in length from the genomic DNAs of a plurality of genomes of different microorganisms or eukaryotes selected from the group consisting of *Fugu rubripes, Caenorhabditis elegans, Saccharomyces cerevisia, E. coli, Aquifex aelitcus, Methanococcus jannaschii, Bacillus subtilis, Haemophilus influenzae, Helicobacter pylori, Neisseria meningiditis, Synechocystis sp. Bordetella pertussis, Pasteurella multocida, Pseudomonas aeruginosa. Borrelia burgdorferi, Methanobacterium thermautotrophicum, Mycoplasma pneumoniae, Archaeoglobus fulgidis* and *Vibrio harveyi;*

(b) combining the nucleic acid fragments from each genome in an amount that is proportional to the complexity and size of the genome of said microorganism or eukaryote, thereby enhancing nucleotide sequence diversity among the combined nucleic acid fragments compared to the diversity of sequences in each genome, (c) inserting the combined fragments at (b) into an expression vector in operable connection with a promoter sequence that confers expression on said fragment in a yeast or bacterial cell, thereby producing a recombinant vector; and (d) introducing the recombinant vector at (c) into a bacteriophage or a yeast cell or bacterial cell such that a nucleic acid fragment contained therein is expressed to produce a polypeptide.

* * * * *